(12) United States Patent
Gelmont et al.

(10) Patent No.: US 8,309,930 B2
(45) Date of Patent: Nov. 13, 2012

(54) METHOD OF LOCAL ELECTRO-MAGNETIC FIELD ENHANCEMENT OF TERAHERTZ (THZ) RADIATION IN SUB-WAVELENGTH REGIONS AND IMPROVED COUPLING OF RADIATION TO MATERIALS THROUGH THE USE OF THE DISCONTINUITY EDGE EFFECT

(75) Inventors: Boris Gelmont, Charlottesville, VA (US); Tatiana Globus, Charlottesville, VA (US); Robert M Weikle, Crozet, VA (US); Arthur Weston Linchtenberger, Charlottesville, VA (US); Nathan Swami, Charlottesville, VA (US); Ramakrishnan Parthasarthy, Houston, TX (US); Alexei Bykhovski, Raleigh, NC (US)

(73) Assignee: University of Virginia Patent Foundation, Charlottesville, VA (US)

( * ) Notice: Subject to any disclaimer, the term of this patent is extended or adjusted under 35 U.S.C. 154(b) by 173 days.

(21) Appl. No.: 12/530,304

(22) PCT Filed: Mar. 5, 2008

(86) PCT No.: PCT/US2008/055962
§ 371 (c)(1),
(2), (4) Date: Sep. 8, 2009

(87) PCT Pub. No.: WO2008/109706
PCT Pub. Date: Sep. 12, 2008

(65) Prior Publication Data
US 2010/0102233 A1 Apr. 29, 2010

Related U.S. Application Data
(60) Provisional application No. 60/904,999, filed on Mar. 5, 2007.

(51) Int. Cl.
*G01J 5/02* (2006.01)
(52) U.S. Cl. .................................. 250/341.1
(58) Field of Classification Search ................ 250/341.1
See application file for complete search history.

(56) References Cited

U.S. PATENT DOCUMENTS
7,608,826 B2 * 10/2009 Itsuji ........................ 250/341.1
2008/0064035 A1 * 3/2008 Densham ......................... 435/6
* cited by examiner

*Primary Examiner* — David Porta
*Assistant Examiner* — Hugh H Maupin
(74) *Attorney, Agent, or Firm* — Sheldon H. Parker Esq

(57) ABSTRACT

A method and apparatus for enhanced THz radiation coupling to molecules, includes the steps of depositing a test material near the discontinuity edges of a slotted member, and enhancing the THz radiation by transmitting THz radiation through the slots. The molecules of the test material are illuminated by the enhanced THz radiation that has been transmitted through the slots, thereby producing an increased coupling of EM radiation in the THz spectral range to said material. The molecules can be bio-molecules, explosive materials, or species of organisms. The slotted member can be a semiconductor film, a metallic film, in particular InSb, or layers thereof. THz detectors sense near field THz radiation that has been transmitted through said slots and the test material.

15 Claims, 20 Drawing Sheets

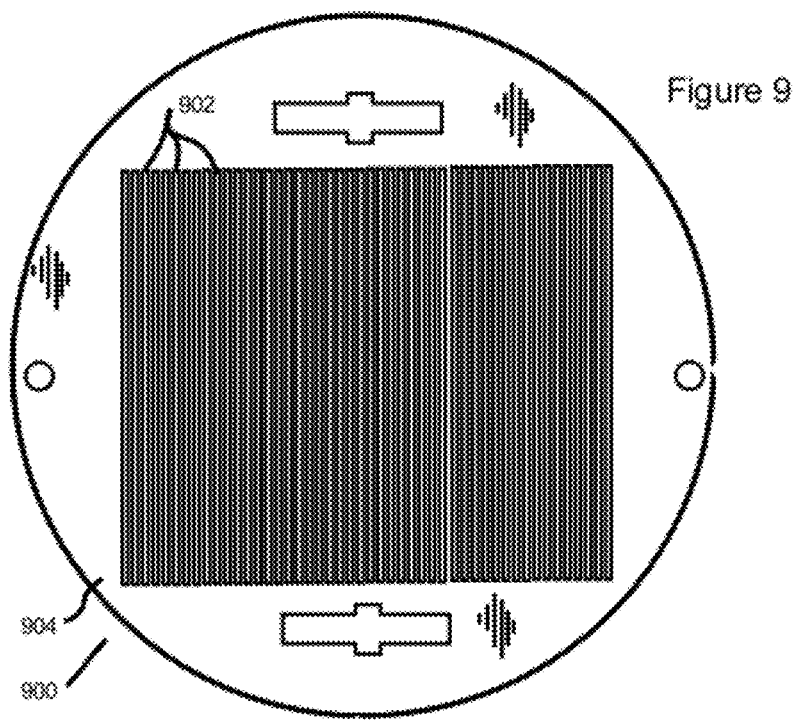
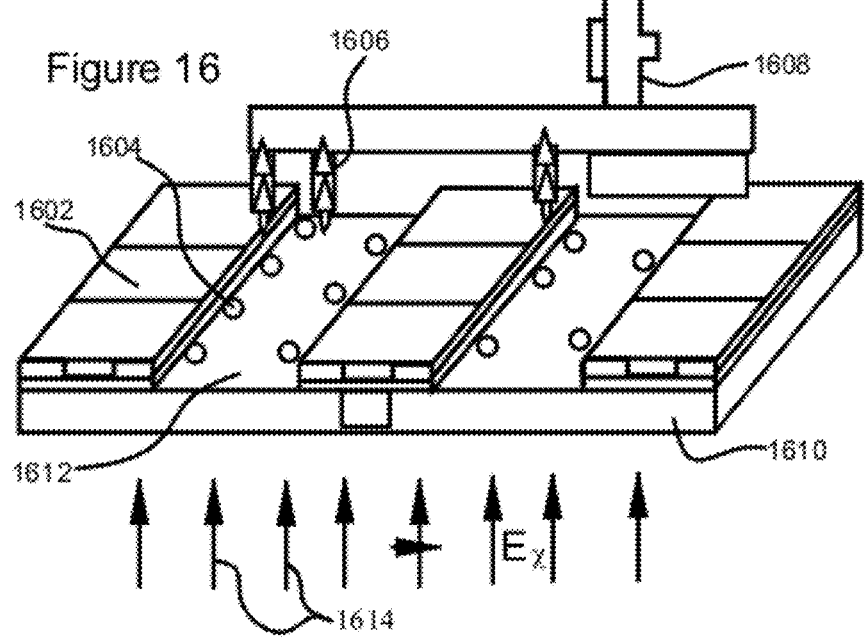

Figure 10
1006                                    1002
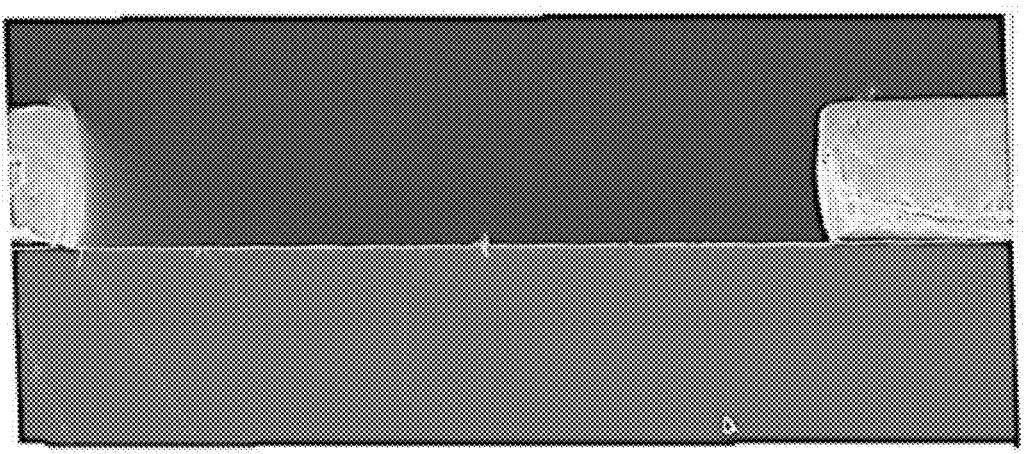
1004
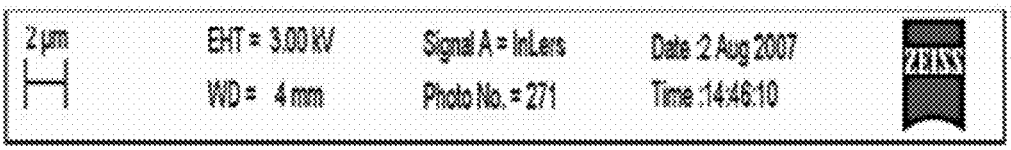

METHOD OF LOCAL ELECTRO-MAGNETIC FIELD ENHANCEMENT OF TERAHERTZ (THZ) RADIATION IN SUB-WAVELENGTH REGIONS AND IMPROVED COUPLING OF RADIATION TO MATERIALS THROUGH THE USE OF THE DISCONTINUITY EDGE EFFECT

CROSS-REFERENCE TO RELATED PATENT APPLICATION

This application is the National Stage entry of PCT/US2008/055962 filed Mar. 5, 2008 and claims the benefit of provisional patent application No. 60/904,999, filed Mar. 5, 2007, having the title "Method of local electro-magnetic field enhancement of terahertz (THz) radiation and related system" the disclosure of which is incorporated herein by reference, as though recited in full.

FIELD OF THE INVENTION

The invention relates to electro-magnetic field enhancement of terahertz radiation in sub wavelength regions and Improved Coupling of radiation to materials through the Use of the discontinuity edge effect and more particularly to the use of slots in materials such as semiconductors and metals for use in THz sensors.

BACKGROUND OF THE INVENTION

At terahertz (THz) frequencies, electromagnetic (EM) fields can be absorbed by optically active internal vibrations of molecules. The capability of THz spectroscopy to detect directly the low-frequency vibrations of weak bonds, including but not limited to hydrogen bonds, is unique in providing information quite different from the visible or IR spectroscopic characterization. This uniqueness opens a large number of applications for THz vibrational spectroscopy in areas such as biomedicine, pharmaceutical analysis, real time monitoring of biological processes, detecting and identification of harmful biological species. A significant advantage of THz spectroscopy is that it is nondestructive to living species. Since each molecule has its own specific internal vibrations, this process can be used to fingerprint, characterize and identify a broad range of molecules. Very recently a THz spectroscopy technique for structural characterization of DNA, proteins and other bio-polymers in diluted solutions was developed by taking advantage of the lower water absorption in the sub-THz vs. IR and far IR regions [1-3].

However, several primary problems impede the development of THz spectroscopy of biological molecules and the application of this technique for characterization, detection, and discrimination between species as well as for the development of new devices for monitoring biological processes. The first problem is that the THz coupling to molecules is not very strong, resulting in poor sensitivity to molecular vibrations. The second problem is low spatial resolution due to the long wavelength of THz radiation (3 mm at 0.1 THz) and diffraction limitation. Thus, the spatial resolution is limited to several mm in the spectral range of 10-30 $cm^{-1}$. This spectral range below 1 THz is especially attractive for practical applications because of low disturbance from the absorption by water or other solvents. In order to increase the sensitivity and reliability of THz fingerprinting techniques, coupling of incident THz radiation to biological or chemical molecules has to be enhanced.

The enhancement of the electric field was demonstrated long ago in optical diffraction by perfect metallic screens. Diffraction by a single slit in a perfect metallic screen was considered by Sommerfield [7]. He studied a case of the incident electromagnetic waves being normal to the screen and proved that the electric field is divergent at the edges of the slit if the incident electric field is perpendicular to the edges. Periodic slot arrays are other possible candidates for increasing the sensitivity. Such arrays were previously used for THz bandpass filters fabricated from lossy metal films deposited on dielectric membranes [8]. Experimental work on enhanced transmission are mostly available at optical and near-infrared frequencies for metallic periodic structures (gratings [9-12] and hole arrays [13-15]). Recently, it has been shown that waveguide resonance and diffraction are the main factors contributing to enhanced transmission of narrow slot subwavelength metallic gratings [12]. The phenomenon of extraordinary optical transmission (transmission efficiency exceeding unity when normalized to the surface of the holes) through hole arrays, first experimentally observed in Ag in 300 nm-1500 nm range [13-14], has been attributed to the resonant tunneling of surface plasmons [14-19] through thin films. Recently, similar studies were conducted in the THz range with hole arrays in films made of metals (Ag-coated stainless steel [20], Al-coated Si wafers [21]) and doped semiconductors (Si [22] and InSb [23]), and also with metallic slot arrays [24] using the perfect conductor approximation).

SUMMARY OF THE INVENTION

The present invention relates to a method and related system to enhance the local electro-magnetic field of THz radiation in sub wavelength regions and to improve the coupling of THz radiation with bio- and chemical materials through the use of the discontinuity edge effects in propagation of radiation in semiconductor or metal slots for application in THz sensors with the spatial resolution much below the diffraction limit.

The electro-magnetic field distribution inside slot or hole arrays was not investigated previously in terahertz range. It has now been found that transmission properties of subwavelength slot arrays are fundamentally different from arrays of holes, since unlike hole arrays, a slot array can support propagating waveguide modes. Thus, increased transmission and local electric field enhancement for transverse magnetic (TM) wave incidence can be obtained through careful choice of materials and design of periodic slot array structures. It has now been found that the enhancement of the THz electro-magnetic field extends across the slots and reaches peak values at the edges because of discontinuity effects. This highly intense localized peak of THz radiation is used in sensors to dramatically improve their spatial resolution and magnify the sensitivity.

An aspect of various embodiments of the present invention may comprise, but not be limited thereto, a novel method and related system to the fundamental problem of improving THz coupling to bio-molecules, explosives, and other materials of interest that have been deposited near the discontinuity edges of a slot or a periodic grating fabricated from semiconductor materials or metals, while simultaneously improving special resolution [4-6]. The improved coupling and spatial resolution are both based on the local EM field and power enhancement near the discontinuity edges with respect to the incident field in structures of slots in a doped semiconductor or metal film or multilayer structures that support modes which locally enhance EM fields. The enhancement mechanism is purely due to the diffraction or discontinuity edge effects in propagation of Terahertz (THz) radiation in subwavelength rectangular slot or periodic structures. It should be noted that theories are provided for background and a full understanding of the technology and not by way of limitation.

The mechanism of coupling of TM polarized THz radiation to the periodic thin film structure consisting of a doped semiconductor with rectangular slot arrays using InSb, Si and gold films are described herein by way of example and not by way of limitation. Transmission properties of subwavelength slot arrays are fundamentally different from arrays of holes, since unlike hole arrays, a slot array can support propagating waveguide modes. Thus, increased transmission and local electric field enhancement for TM incidence can be obtained through careful choice of materials and design of periodic slot array structures. The enhancement of the THz electro-magnetic field extends across the slots and reaches peak values at the edges because of discontinuity effects.

The vector of the electric field E is directed perpendicular to the slots. This approach leads to a new mechanism for sub-wavelength THz imaging sensing with sub-micron spatial resolution.

This method of local enhancement has been discovered using a rigorous mathematical solution of Maxwell's equations for doped semiconductor and metal structures with sub wavelength one dimensional slot arrays subjected to THz radiation. Using InSb as an example, an EM field enhancement of over 30 near the slot edges translates into a 1000 fold increase in power.

The "edge effect" at sub-THz frequencies caused by the effects of the discontinuity of the present invention, is a very important new result that guides the novel device design. In one embodiment, the bio- or chemical material is embedded in the regions of the slot edges where the EM field enhancement is generated. Other modifications include semiconductor or metal films and multilayer structures with slots of different periodicity and geometry with bio- or chemical material embedded at locations of EM field enhancement. The bio- or chemical material can also be delivered to the slots using microfluidic channels. The enhanced coupling to biological or chemical material inside the chip at particular frequencies within THz gap (approximately 0.1-10 THz) results in more significant changes to the transmitted and reflected spectra that can be applied to enhance the sensitivity and selectivity of bio- and chemical detection.

One example of an important practical application of this invention is the development of a simple, all optical, appertureless, subwavelength transmission THz sensor with the spatial resolution much below the diffraction limit and integrated with a microfluidic channel chip for a sample material. The imaging mechanism of the present invention, integrated with a "lab-on-a chip" device, is the heart of a sub-wavelength THz microscopic sensor.

An aspect of the present invention is a grating structure with optimized periodic sub-wavelength geometries and integrated with a microfluidic chip for bio material analyte.

Another aspect of the present invention is an inexpensive microfluidic chip made from plastic and integrated with a thin film grating to dramatically enhance sensitivity and spatial resolution. In such an instrument, the other crucial component is a miniature detector assembly with micron size antenna mounted on the translation stage to probe the spatial distribution of a THz signal in a near field configuration.

A further aspect of this invention is an integration of these central components of a proposed sensor with a THz source through the optical focusing system.

The instrument is capable of collecting THz-frequency signatures from microscopic biological or chemical molecules. The upper frequency limit of practical application of discovered mechanism for the local EM field enhancement is determined by the condition $d<\lambda$, where $\lambda$ is the wavelength of radiation and d is the structure periodicity.

The prototype of a miniature THz detector consisting of a Schottky diode integrated with a circuit and a sub-micron beam lead probe has been designed and fabricated. The integration of the detector assembly with the translation stage has been designed. The periodic slots structure has been fabricated using the photolithographic process and electroplating. The microfabrication processes have been optimized to obtain high sharpness at the edge of the slots. The technology to fabricate and characterize microfluidic channels for biological molecules was also demonstrated.

This novel detection platform can be applied to, but not limited thereto, the development of a new class of resonant, highly sensitive and selective portable bio- and chemical devices for biochemical, medical and military applications.

Some exemplary novel aspects that may be associated with various embodiments of the present invention method and system may comprise, but not limited thereto, the following:

The method of detection the spectroscopic signatures of bio-molecules or other materials of interest, such as explosives, using the local EM field enhancement with respect to the incident field within semiconductor or metallic slot or hole arrays. This enhancement leads to increased coupling of EM radiation in the THz spectral range to materials of interest and, therefore, results in dramatic improvements to the sensitivity, selectivity, reliability and spatial resolution of THz detection systems.

(2) Criteria for optimizing the selection of materials and properties appropriate for the local distribution of THz radiation suitable for the method as (1).

(3) Design of a periodic structure of slots to support a set of THz modes that locally enhance EM fields for the method as (1).

(4) Application of the periodic structure of slots to locally enhance THz coupling to biological, explosive, or other materials of interest in solid or fluidic form, with the material immobilized on the surface, trapped at slot edges, or scanned across a microfluidic chamber.

(5) Application of the periodic structure of slots scanned the slots across the material sample to enhance local coupling and thereby improve the chemical resolution and sensitivity of the detector to THz imaging.

(6) Application of the periodic structure of slots to detectors that include miniaturized THz near-field sensing.

(7) Application of the collimated beam of a polarized THz radiation to illuminate a structure from rectangular slots in a thin metallic or doped semiconductor film.

(8) Developing a grating structure with optimized periodic sub-wavelength geometries.

(9) Integration of THz radiation with an inexpensive (disposable) microfluidic chip containing sample materials in aqueous or biological native state, made from plastic or other materials transparent in the THz range.

(10) Application of the thin film slot grating integrated with the microfluidic channel with the sample material to be tested where it is illuminated with the terahertz energy.

(11) Integration of THz radiation with a microfluidic network of channels of nanoscale thickness for purposes of washing, sorting and pre-concentration of samples to permit real-time THz detection and characterization at improved sensitivities.

(12) Application of the integrated THz micro-detector assembly that is composed of three essential parts, i.e. a micron/sub-micron probe (antenna) that is connected to a miniature detector and control circuit with the corresponding impedance matching network to achieve the precise detection of the electric field in the near-field configuration.

(13) Application of mounting the detector assembly on the stage, which can provide precise (with resolution less than 1 μm) scanning over the sample under test along XYZ direction with nanometer accuracy controlled by the control circuit.

(14) Application of microscopic device for precise positioning of a micron probe in close vicinity of a slot structure outdoing interface.

(15) Alternatively, application of an electric (capacitive) mechanism for precise positioning of a micron probe in close vicinity of a slot structure outdoing interface.

(16) Application of reduced amount of material for characterization.

(17) Application of a linear array of miniature detectors integrated with scanning mechanism for a THz imaging.

The invention is illustrated by the example structure consisting of a one-dimensional array of rectangular slots with the period less than the wave length of applied EM radiation in a thin doped InSb film with a free electron concentration of $1.1 \times 10^{16}$ cm$^{-3}$. This is not to be construed in any way as imposing limitations upon the scope of the invention. Structures with slot arrays or hole arrays of different periodicity and different geometry can be used as well. Different materials such as semiconductor films or metallic films can be used separately or in combinations as in multilayer structures.

Applications might include simple microscopic sensors for detecting traces of particular material at the nanograms level in a solid form or in dilute solutions in water or other analytes; microscopic sensors combined with microfluidic channels for monitoring biological processes; microscopic sensors with linear detectors array and two dimensional scanning as THz imaging instruments.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

In accordance with an embodiment of the invention, an enhanced THz coupling to molecules is achieved by depositing a test material near the discontinuity edges of a slotted member, enhancing the THz radiation by transmitting THz radiation, having a vector directed perpendicular to the slots of the slotted member and illuminating molecules of the test material with the enhanced THz radiation transmitted through these slots. This method results in producing an increased coupling of EM radiation in the THz spectral range to the material.

In accordance with another embodiment of the invention the enhanced THz radiation is an EM field of terahertz radiation in a submicron region, and the THz vibration absorption by the test material is analyzed. The molecules can comprise bio-molecules, organic molecules, or an explosive.

In accordance with a further embodiment of the invention the slotted member is selected from the group comprising doped semiconductors, metal films, and multilayer structures that support modes that locally enhanced EM fields, and near field sensing of THz radiation from the molecules. Increased coupling and spatial resolution are both based on the local EM field and power enhancement near the discontinuity edges with respect to the incident field in slotted structures.

In accordance with a further embodiment of the invention an EM field enhancement is generated at the edges of the slots and a bio- or chemical material is embedded at the location of the EM field enhancement. THz radiation is transmitted through the slots and bio- or chemical material at the location of EM field enhancement and the near field THz radiation that has been transmitted through the slots and has illuminated said bio- or chemical material at the location of EM field enhancement is then sensed. The transmission of THz radiation through the slots increases the degree of the coupling of EM radiation in the THz spectral range to materials of interest by transmitting THz radiation through an array of openings, to detect the spectroscopic signatures of said bio- or chemical material. Near field scanning with a THz antenna, of transmitted radiation of the slotted member from sample material near the discontinuity edges can be used.

In accordance with a still further embodiment of the invention the increase in coupling of EM radiation in the THz spectral range to weak bonds in molecules, is achieved by depositing a material of biological or chemical molecules near the discontinuity edges of slots of a slotted member, and transmitting THz radiation through the slots and illuminating the molecules with the transmitted THz radiation. The slots are periodic structures with the coupling increase being due to the diffraction or discontinuity edge effects in propagation of THz radiation in subwavelength rectangular slots of the slotted member, which is fabricated from semiconductor materials, metals, or combinations thereof. The near field THz radiation is transmitted through said slots and said bio- or chemical material which can be selected from the group comprising explosives, toxic materials, living organisms and pharmaceuticals, is then sensed.

In accordance with a further embodiment of the invention the changes of dielectric properties of bio-materials in biophysical processes, is monitored. The property is selected from the group comprising denaturation of DNA, folding-unfolding of proteins, and structural conformational changes of biomolecules in interactions with drugs. A GHz signal is generated and the GHz radiation converted to THz radiation with a frequency multiplier. The THz radiation is collimated for transmission through the slots and illumination of the molecules with the transmitted THz radiation. An EM field enhancement is generated at the edges of the slots, selectively detecting enhanced THz transmitted through the bio-materials at the slot edges. The selectively detected enhanced THz radiation is monitored to determine changes of dielectric properties of bio-materials in biophysical processes.

In accordance with a further embodiment of the invention an all-optical, apertureless instrument, free of mechanical tips or probes to contact testing material is used for analysis. The instrument comprises a slotted member, a source of THz radiation, and an analyte material embedded at least at the edges of the slots of the slotted member. The analyte material is molecules in dilute solutions with the molecules selected from the group comprising monolayers of biological material and cancer cells.

In accordance with a further embodiment of the invention an integrated THz micro-detector assembly comprises a sub-micron probe connected to a miniature bolometer detector and control circuit with a corresponding impedance matching network and is used to achieve the precise detection of the electric field in the near-field configuration. The sub-micron probe is mounted on a stage and positioned for near field scanning, with a resolution of less than 1 nm, over the sample under test along XYZ direction with nanometer accuracy controlled by said control circuit. Preferably the sub-micron probe is positioned within 2 microns of the sample.

In accordance with a further embodiment of the invention the coupling of THz radiation to molecules in the analyte sample is increased by using a slotted member, consisting of an array of rectangular slots or elongated holes, positioned between said source of EM radiation in the THz spectral range and the materials of interest. The slotted member can be an array of spaced strips of metal, semiconductors, or layers thereof and selected from the group comprising thin InSb thin film, thin Si thin film and a thin Au thin film and combinations thereof.

In accordance with a further embodiment of the invention a device for sub-wavelength THz imaging sensing with sub-micron spatial resolution consists of means for generating THz radiation, a slotted structure with slots of a predetermined periodicity and geometry, a translation stage, a miniature detector assembly and at least one THz radiation sensor. The detector assembly is a chip about 1 mm wide and 1.5 mm long having a beam lead micro-tip with a length of about 60μ. long, a tip length of about 15 μm, a tip width of about 15 μm, and a tip of about 0.6 μm. The detector further has a micron size antenna mounted on the translation stage, to probe the spatial distribution of a THz signal in a near field configuration. The THz radiation sensor(s) are positioned to receive THz radiation from the slots. The slotted structure can be a one-dimensional array of rectangular, or elongated, slots with a periodicity of less than the wave length of applied EM radiation in a doped InSb thin film. A fluidic member having microfluidic channels, delivers bio- or chemical material to the slots through the microfluidic channels. The microfluidic chamber comprises a network of micro-channels of nanoscale thickness, and means for at least one of washing, sorting and pre-concentration of samples to attain real-time THz detection at improved sensitivities. The micro-channels can be about 5-50 μm wide, 1 μm deep, 1-2 μm long, and are in a 10-50 μm substrate of polydimethylsiloxane (PDMS) or polymethylmethacrylate (PMMA), or other material, that is transparent to THz radiation.

In a further embodiment of the invention an optical device, such as a THz microscope, comprises an apertureless, sub-wavelength transmission THz sensor with the spatial resolution substantially below the diffraction limit and having a source of THz radiation, a slotted member with substantially rectangular or elliptical slots of a predetermined periodicity and geometry, at least one THz radiation sensor positioned to receive near field THz radiation transmitted through said slots at the slot edges and means to optically focus the THz radiation through the analyte. An EM field enhancement is generated at the edges of the slots, with a bio- or chemical material embedded at the location of EM field enhancement. An integrated microfluidic channel chip, comprises a network of channels of nanoscale thickness, delivers a sample material to the slotted member. The slots have a width less than the wavelength of the THz radiation and a length greater than the wavelength of the THz radiation and d<μ, where μ is the wavelength of radiation and d is spacing from the distal edge of one slot to the proximal edge of the next slot. Means are provided to collimate and polarize the THz radiation and the THz radiation can be a collimated beam of a polarized radiation and illuminates an analyte through rectangular slots in a thin metallic or doped semiconductor film. The analyte materials are in solid or fluidic form, and are embedded on the surface of the slotted member, trapped at slot edges, embedded in slots, or scanned across a microfluidic chamber. An integrated THz microdetector assembly comprising a micron/sub-micron probe connected to a miniature detector and control circuit, said control circuit having a corresponding impendence matching network to achieve the precise detection of the electric field in the near-field configuration can be incorporated. The micro-detector assembly, a linear array of miniature detectors integrated with said scanning mechanism for THz imaging of analytes, is mounted on a stage member to provide precise scanning, with resolution less than 1 nm, over the sample under test along XYZ direction with nanometer accuracy controlled by the control circuit.

In a another embodiment of the invention a monitoring system for monitoring changes of dielectric properties of materials comprises a THz source, with a GHz signal generator, a frequency multiplier, and a power supply for said source; at least one collimating member; a periodic slot chip; a detector assembly chip and a motorized XYZ stage with controller. The detector assembly chip is mounted on a stage for XYZ movement with respect to said periodic slot chip, for detecting and monitoring THz radiation that is transmitted through slots in the periodic slot chip.

as a function of a coordinate x (μm) across a slot for the structure parameters d=381 μm, s=55 μm, h=4 μm and for the wavelength λ=714 μm. Note the majority of the enhancement takes place at the slot edges i.e. around (−s/2) and (s/2).

Figure 2:
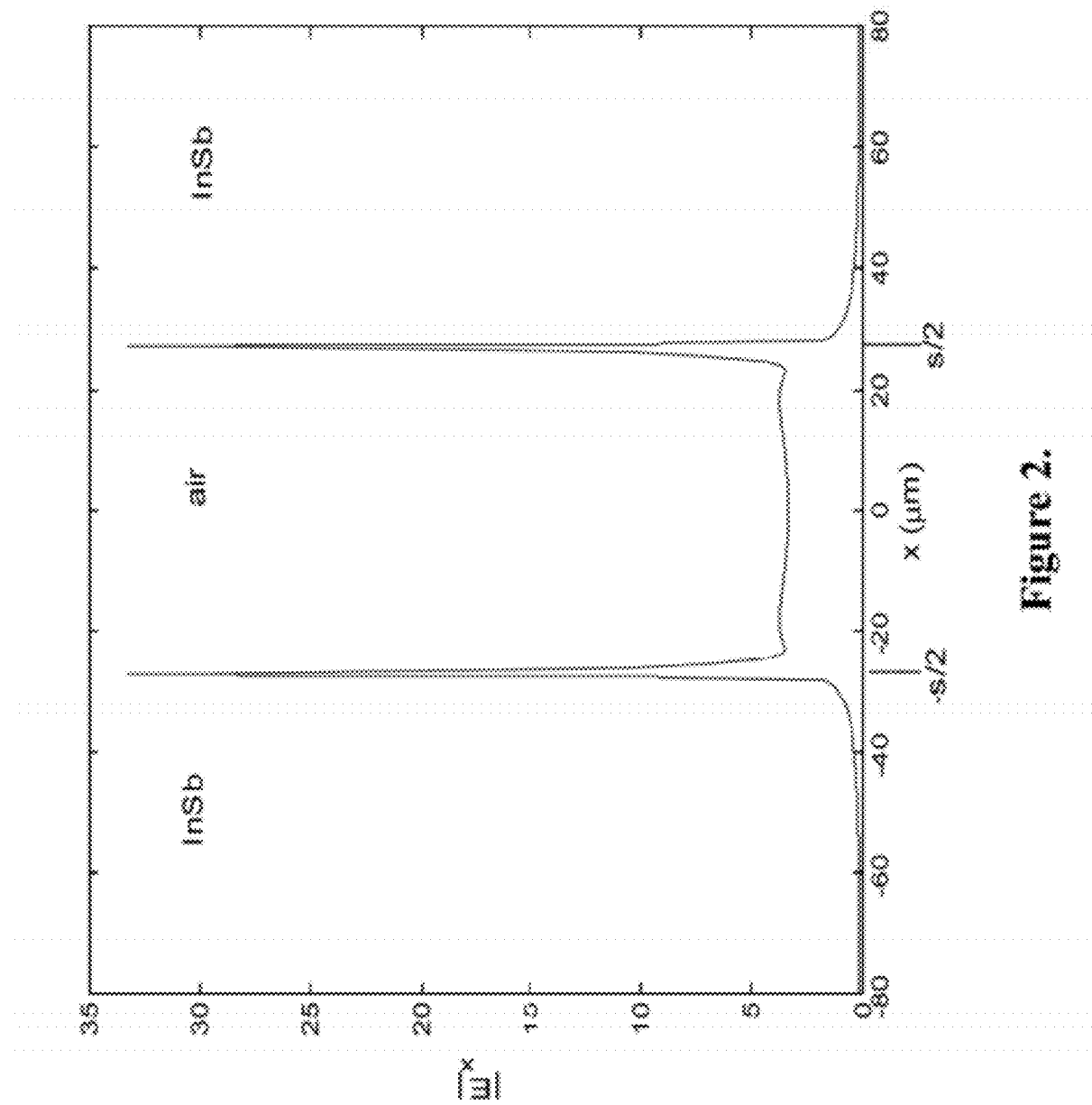
FIG. 2. Electric field enhancement, $$\left|\frac{E_x^i}{E_0}\right|,$$
Figure 3:
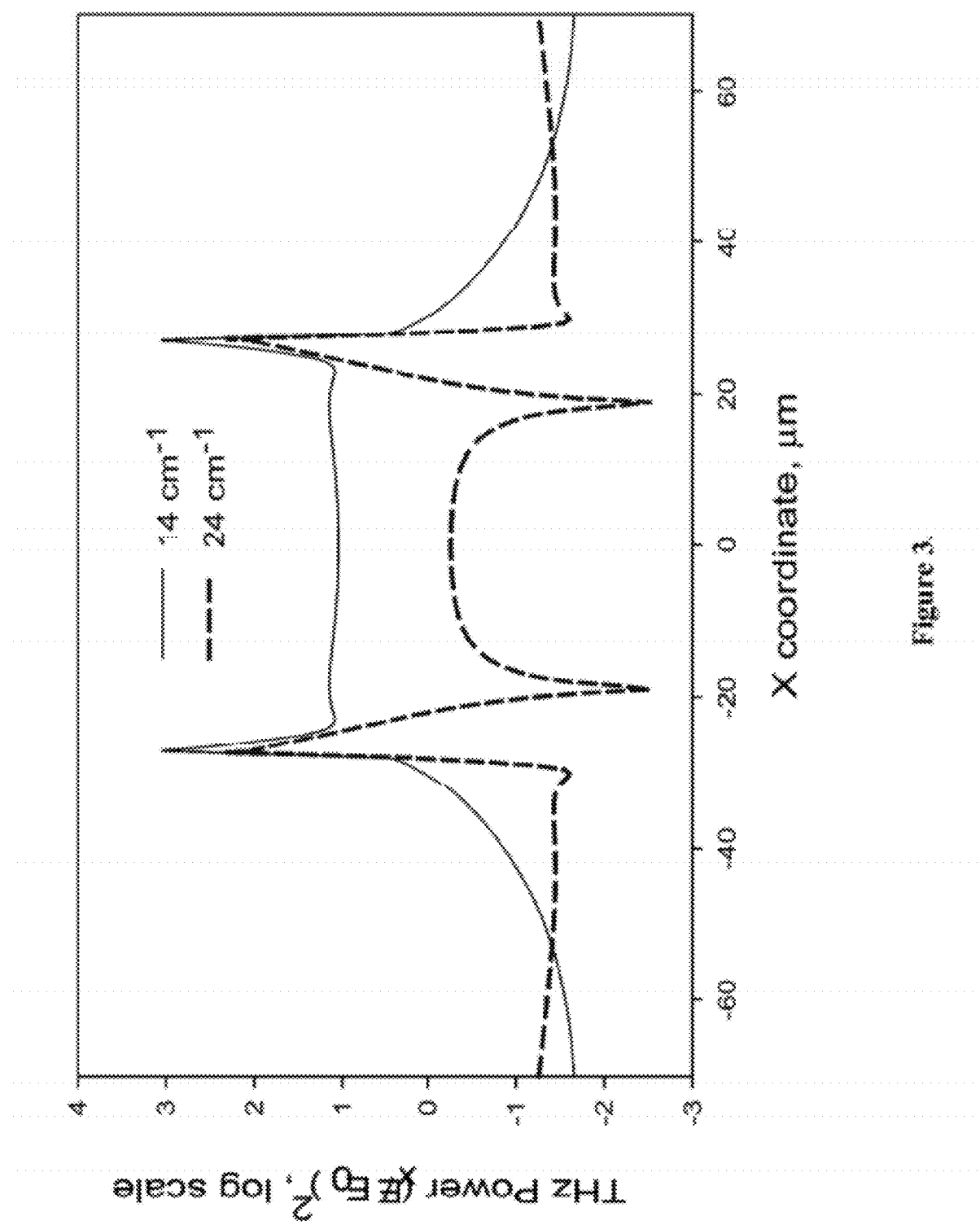

FIG. 3. THz power, $(E_x/E_o)^2$, enhancement as a function of a coordinate x (m) across a slot for the structure with the same parameters as in FIG. 2 at two frequencies 14 cm$^{-1}$ (the wavelength=714 m) and 24 cm$^{-1}$.

Figure 4:
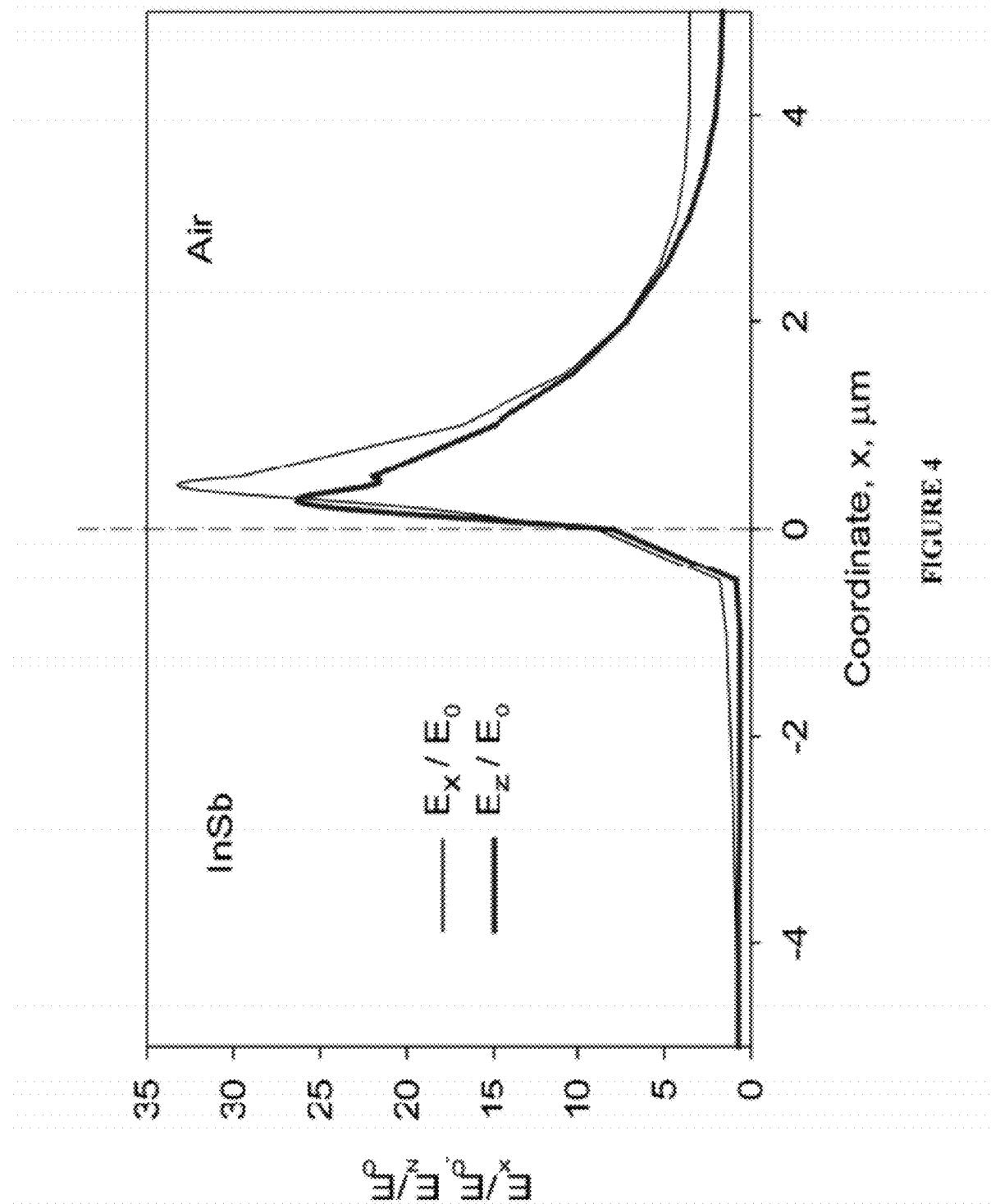

FIG. 4. The edge effect for two components of electric field $E_x$ and $E_z$.

Figure 5:
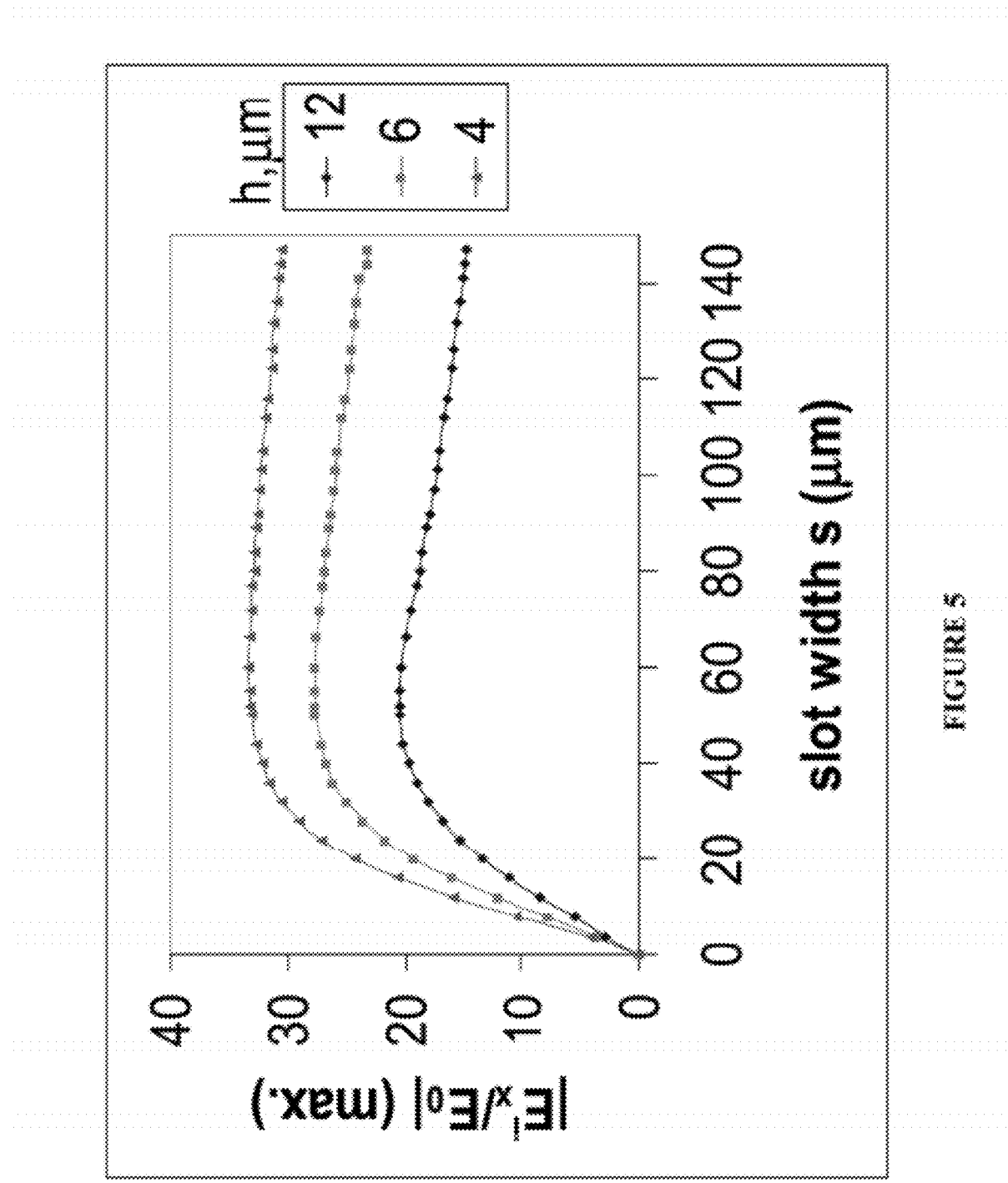

FIG. 5. Plot of maximum electric field enhancement, $$\left|\frac{E_x^i}{E_0}\right|(\text{max.}),$$

at the incident interface and around slot edges as a function of a slot width, s, with d=381 m, and =714 m, for different h values (h=12 m, 6 m and 4 m).

Figure 6:
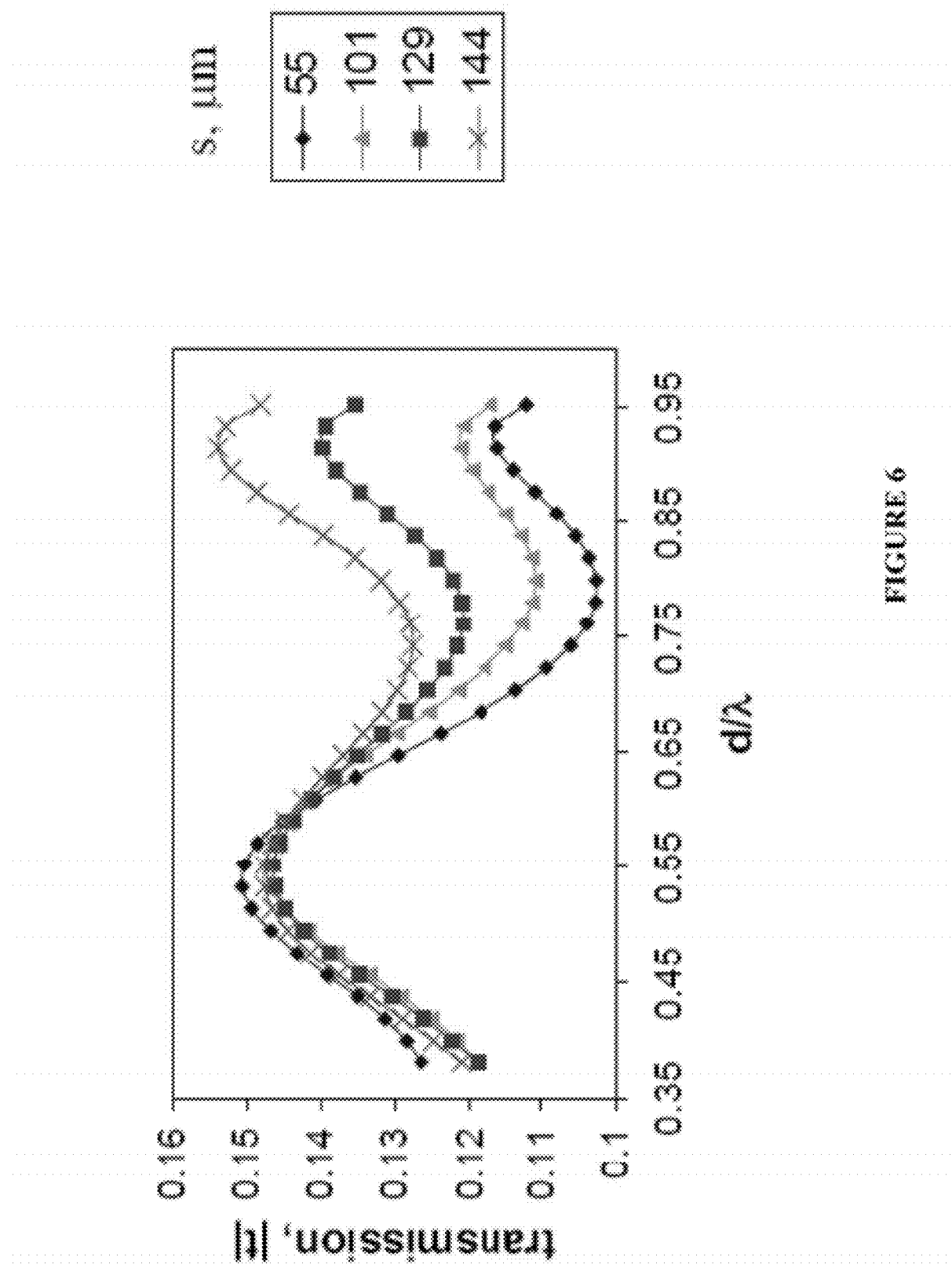

FIG. 6. Far field transmission, |t|, as a function of d/λ for different values of a slot width, s. Here d=381 μm, h=12 μm.

Figure 7A:
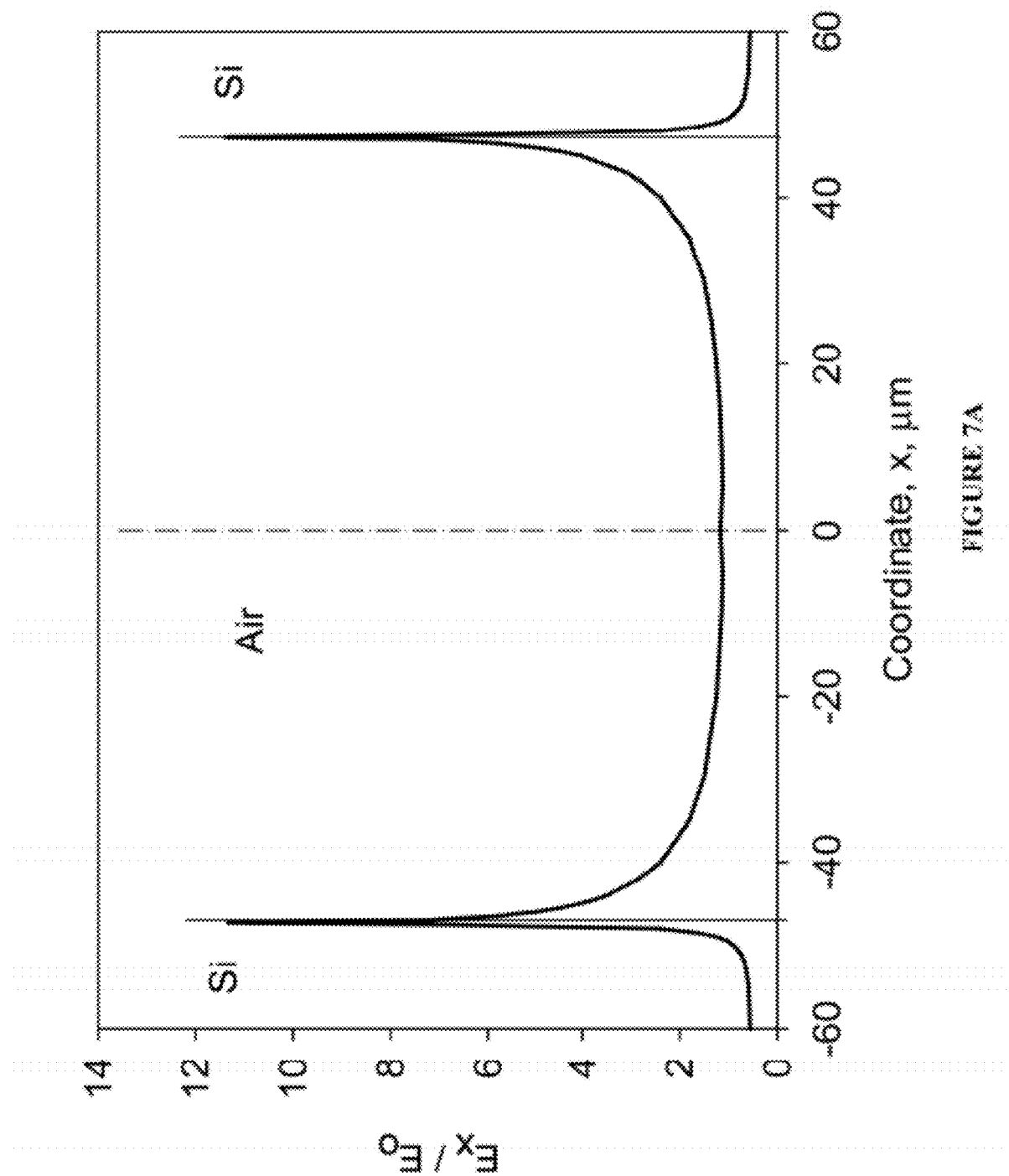

FIG. 7A. The edge effect in periodic structures made of a Si film: d=251 μm, s=95 μm, and h=4 μm, and of a gold film.

Figure 7B:
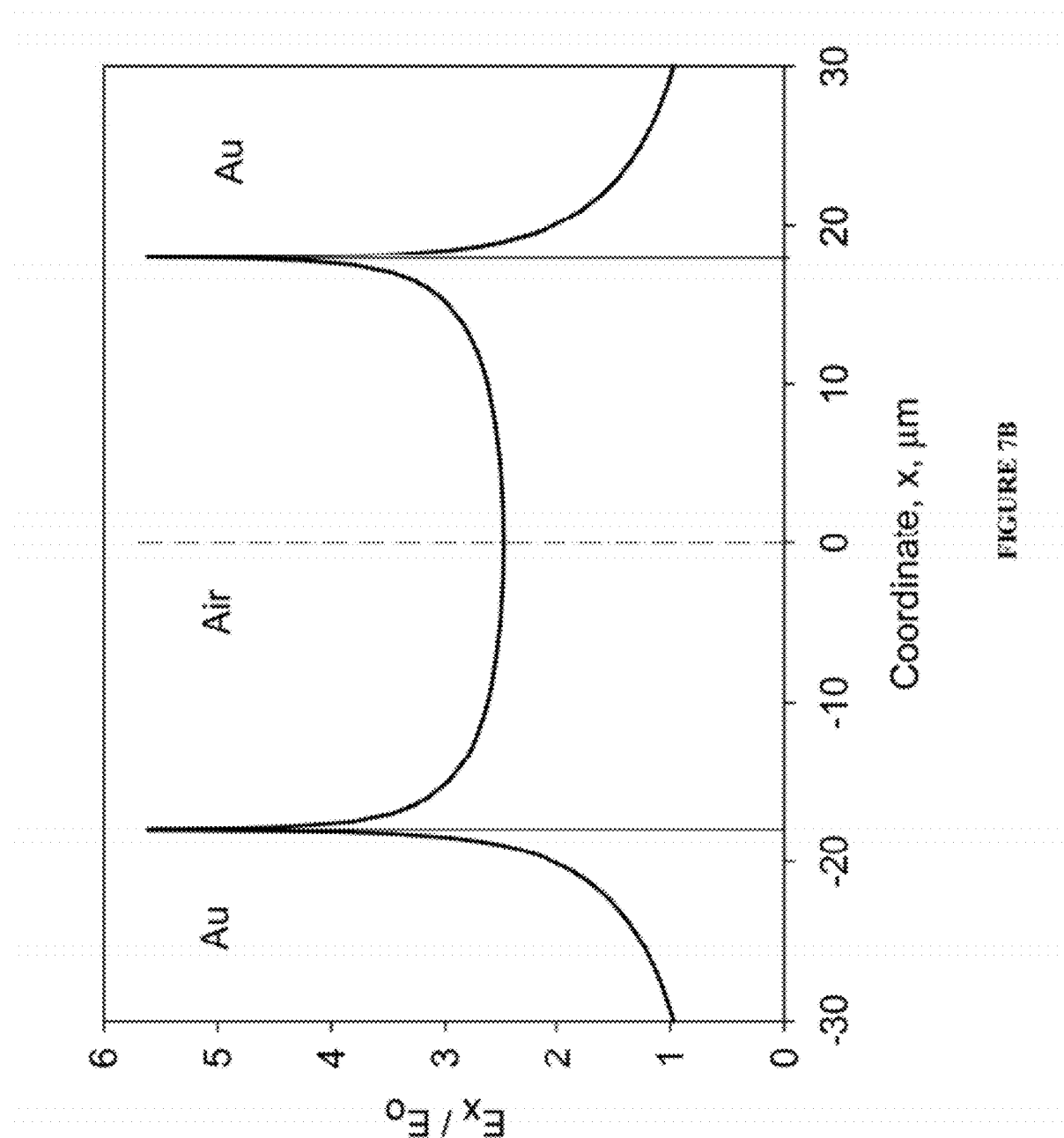

FIG. 7B. The edge effect in periodic structures made of a Si film d=251 μm, s=36 μm, and h=4 μm.

Figure 8:
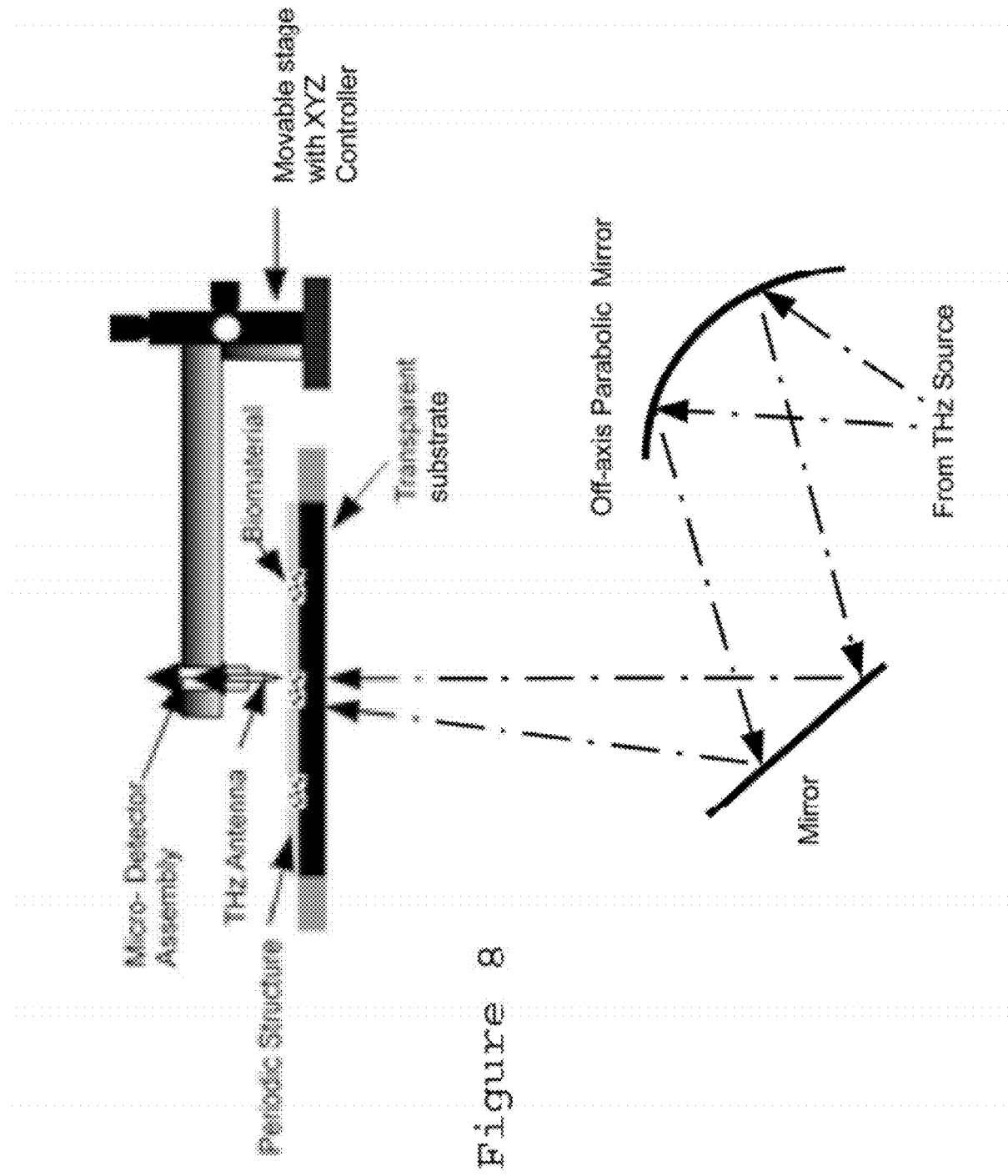

FIG. 8. A diagrammatic illustration of a THz microscopic sensor.

FIG. 9. The periodic slot structure made of gold on the silicon wafer fabricated using the photolithographic process and electroplating. The yellow parts are gold and the dark parts are air slots of 55 μm. The similar periodic structure was fabricated on a quartz substrate and using polydimethylsiloxane polymer substrate.

FIG. 10. A SEM picture of one gold slot. The edge extrude is 0.5 μm.

Figure 11A:
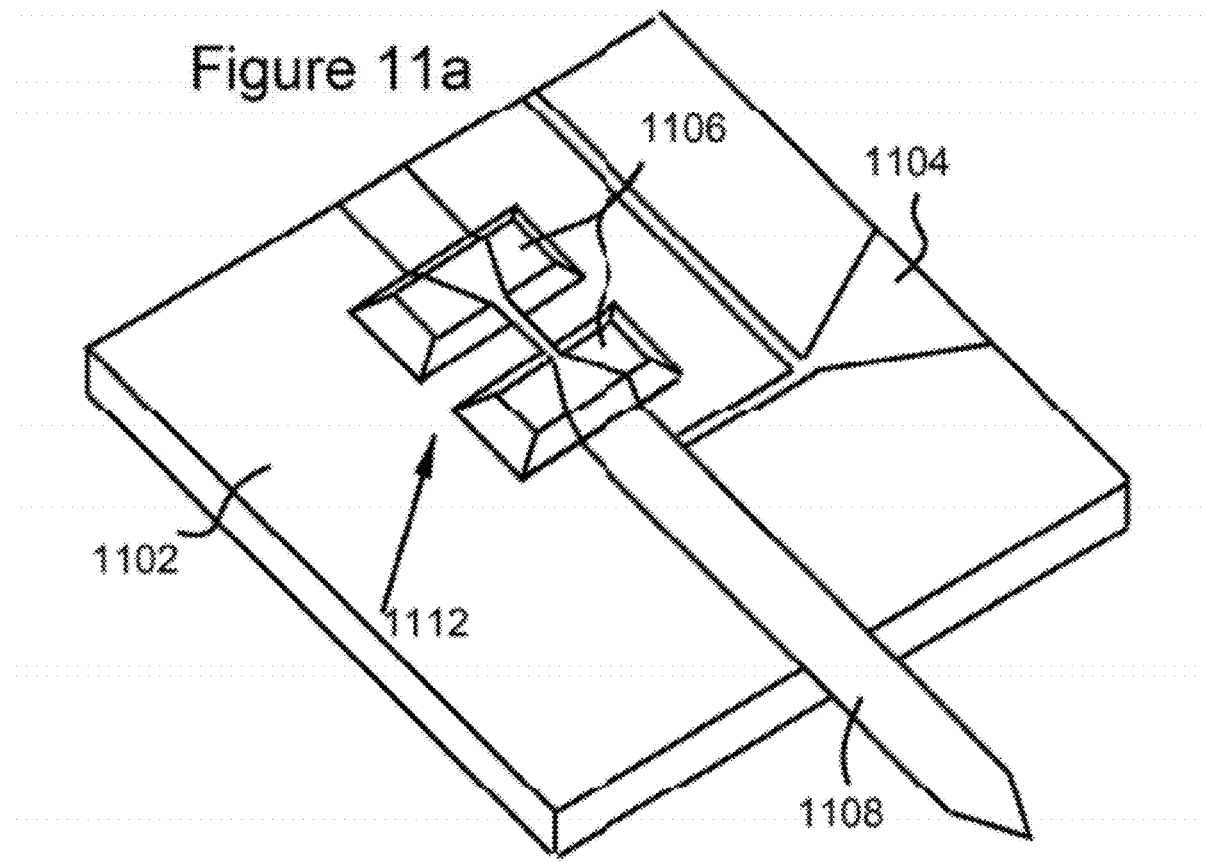

FIG. 11A. Concept of integrated probe with Schottky diode detector.

Figure 11B:
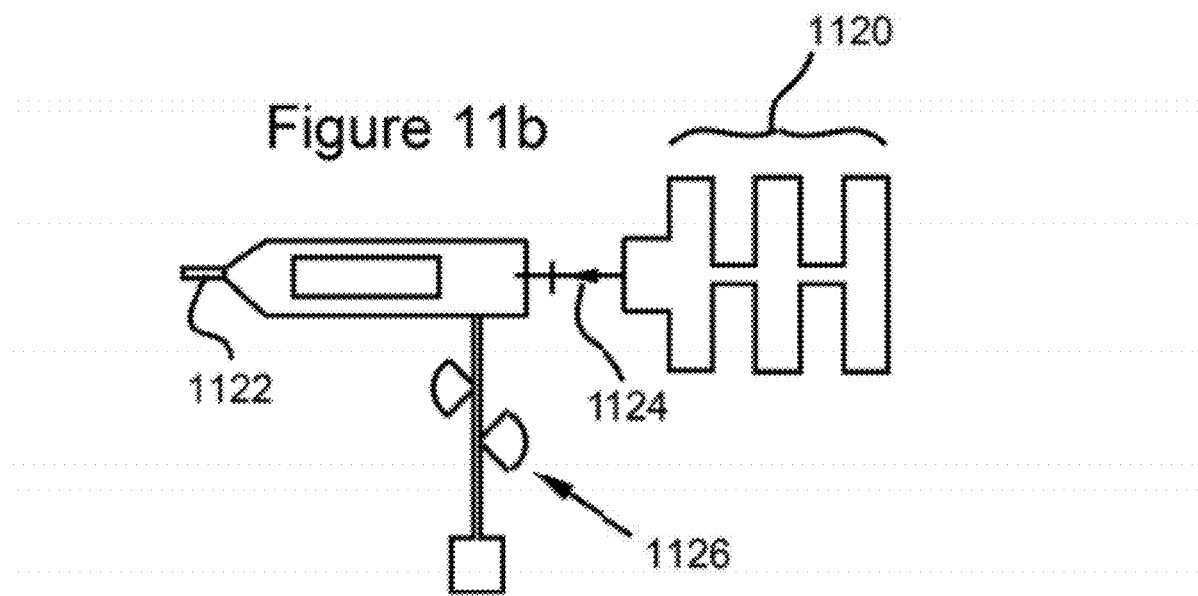

FIG. 11B. Prototype sensor circuit with planar probe. The position for the diode detector between the probe and lowpass filter is indicated.

Figure 12:
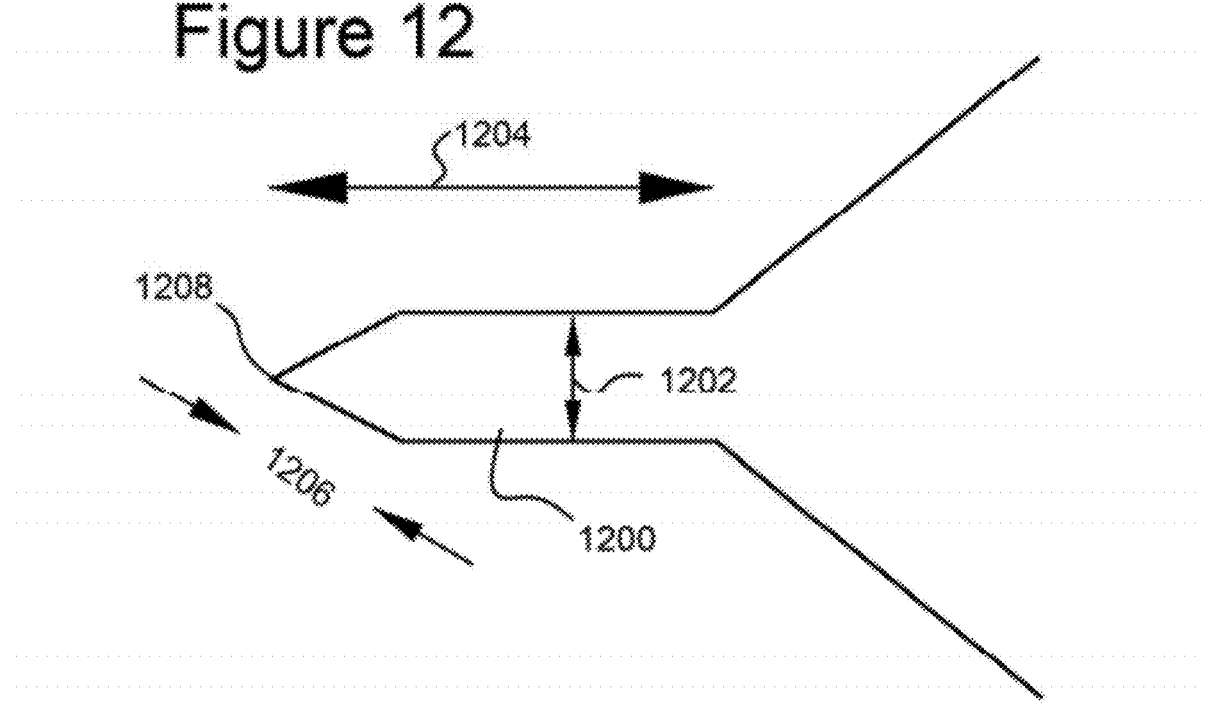

FIG. 12. Beam lead structures fabricated on an ultra-thin (5 μm thick) silicon chip.

Figure 13:
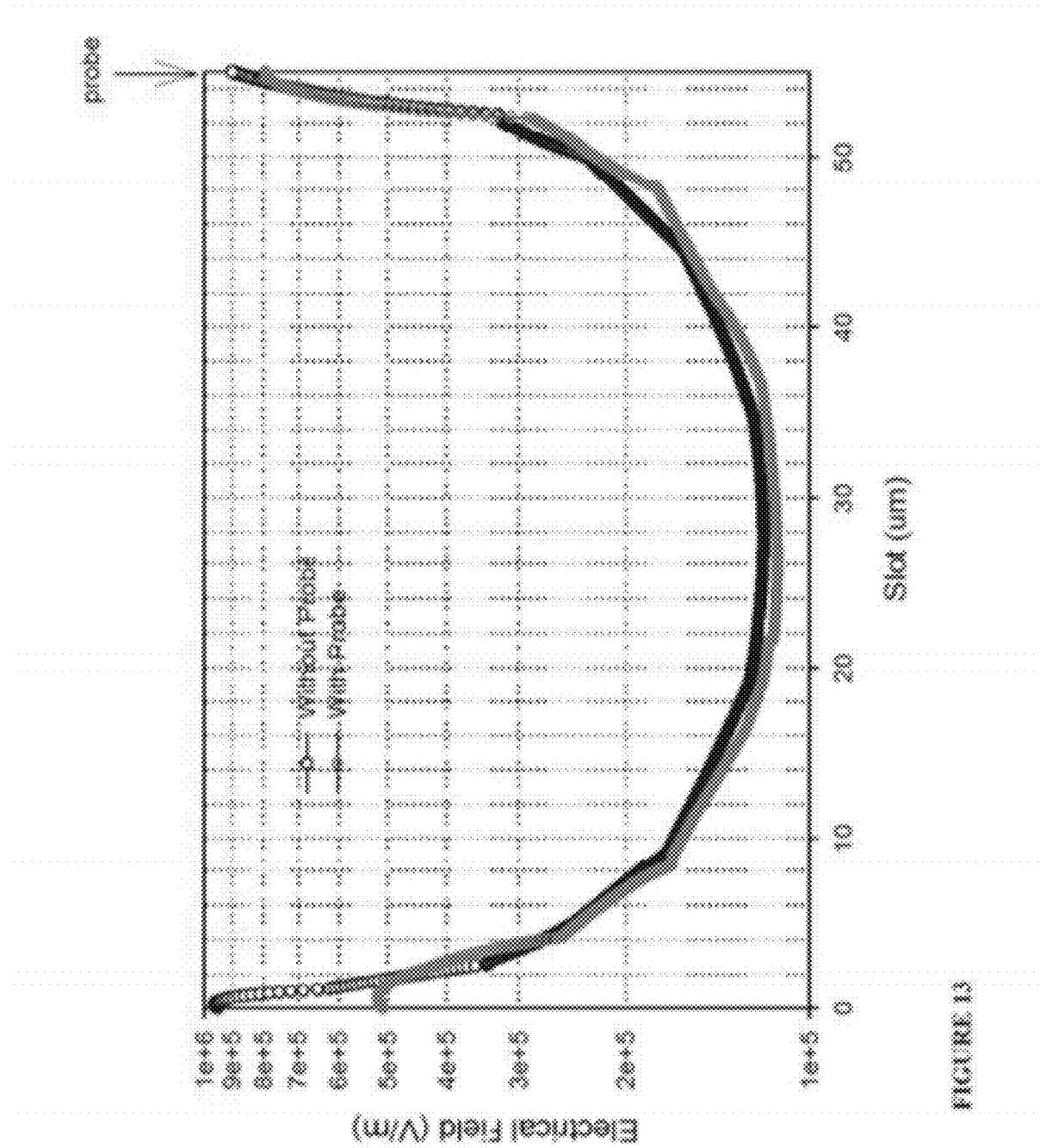

FIG. 13. The electrical field distribution along the cross section of one slot with and without the detecting probe present. The distance between the probe and the slot surface is 1 μm.

Figure 14:
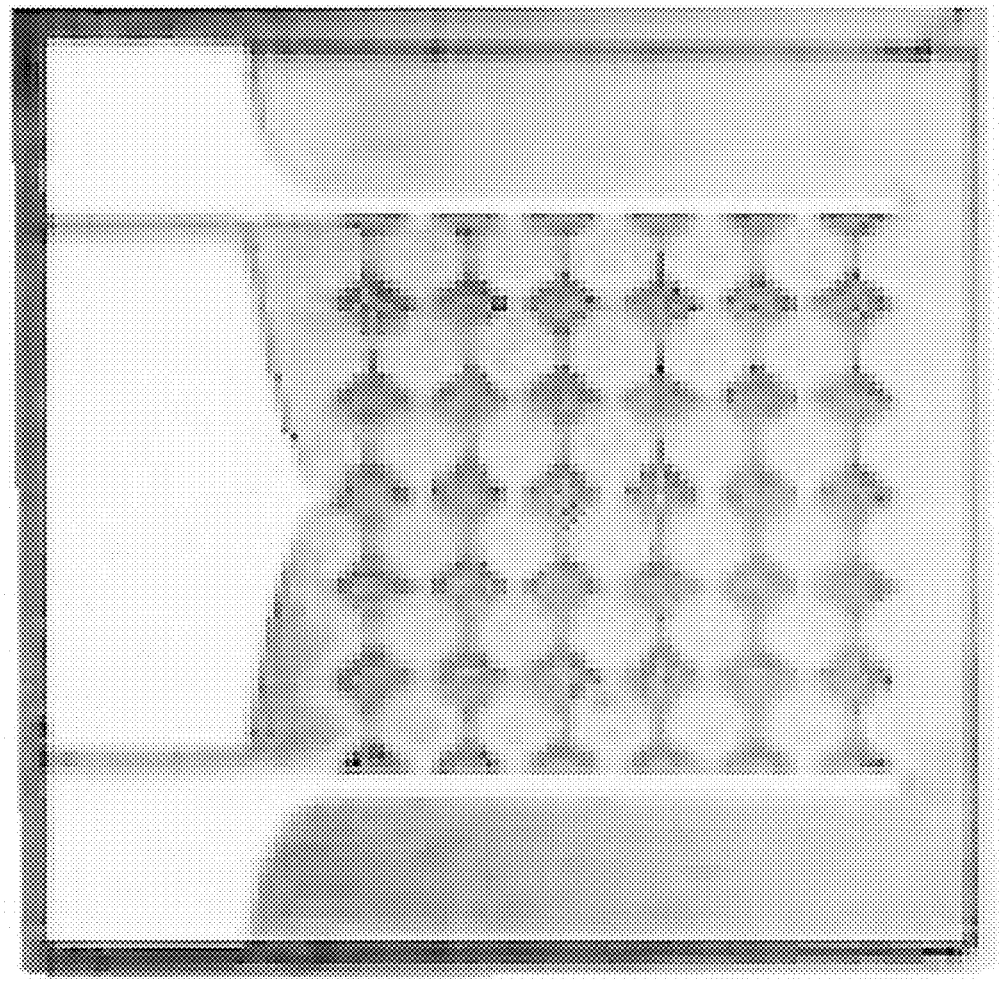

FIG. 14. Array of detectors for operation at 1.6 THz. The spacing between adjacent elements is 40 μm and the substrate material is quartz [28].

Figure 15:
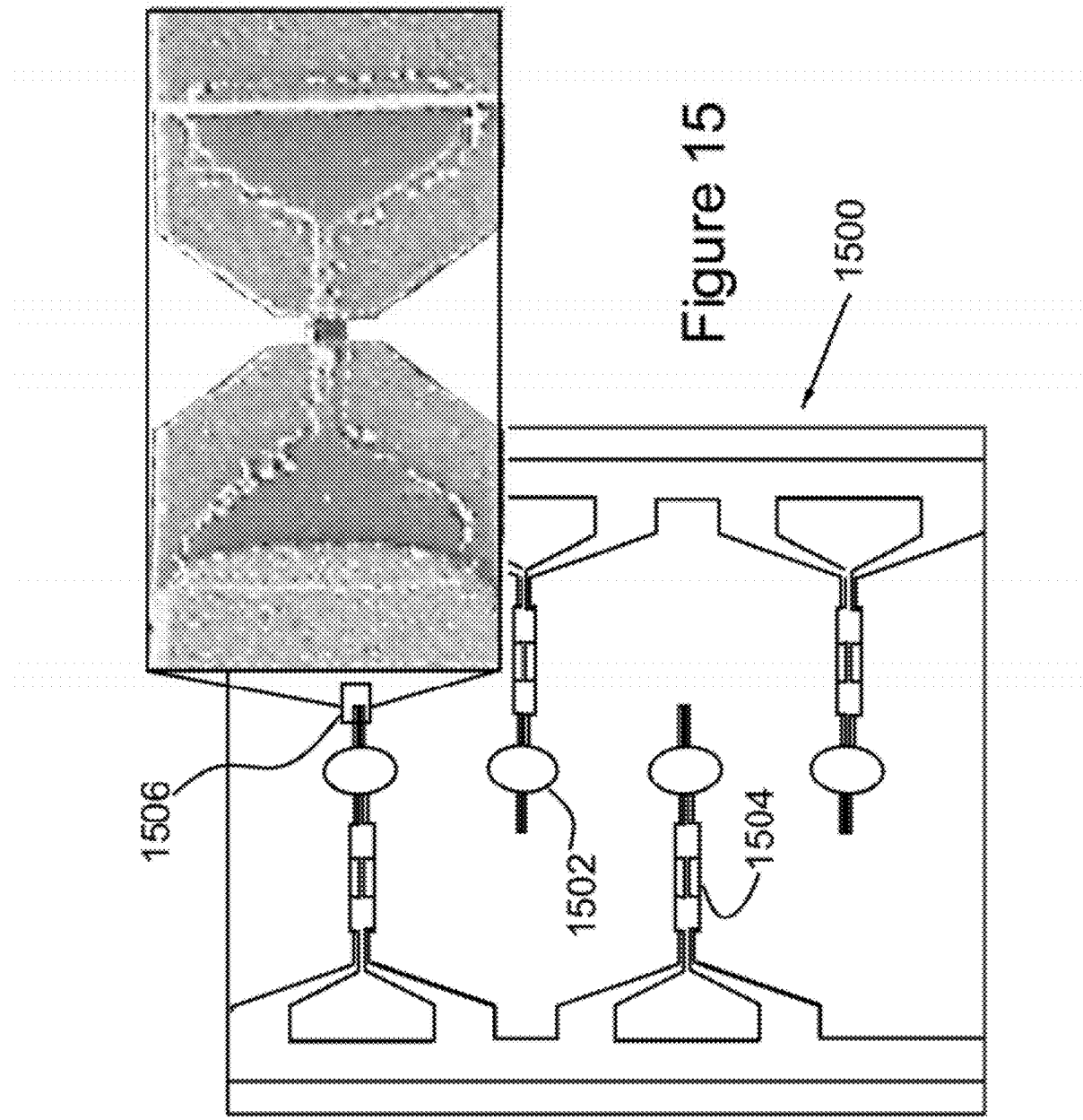

FIG. 15. Miniature detectors (nanometer-scale bolometer) integrated with planar antennas for operation at 600 GHz [29].

FIG. 16. A preferred embodiment for applying the periodic slots to increase the THz coupling to molecules across the sample area, through the use of a piezo-stage to scan the light exiting the slot edges across the samples and place the detector in close proximity to the slots and sample. A detector assembly is combined with a sample or microfluidic channel (5-50 μm wide, 1 μm deep, 1-2 cm long, with a 10-50 μm backing support to enable handing) filled with biomaterials. A 2-5 μm Au edge layer is patterned on the top edge of channel. Not in scale.

Figure 17:
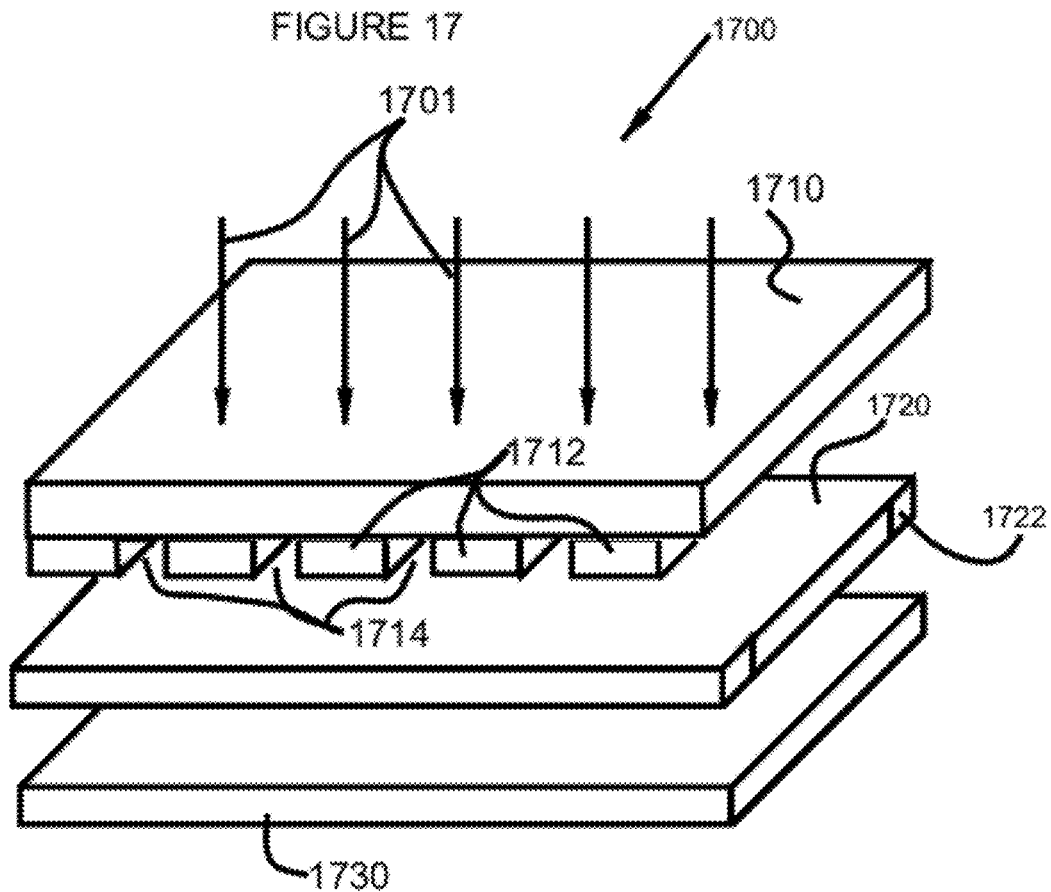

FIG. 17. Example of assembly for integrating periodic microfluidic structure with translatable miniaturized detectors (not in scale) for monitoring changes of THz dielectric properties of bio-materials in solutions.

Figure 18A:
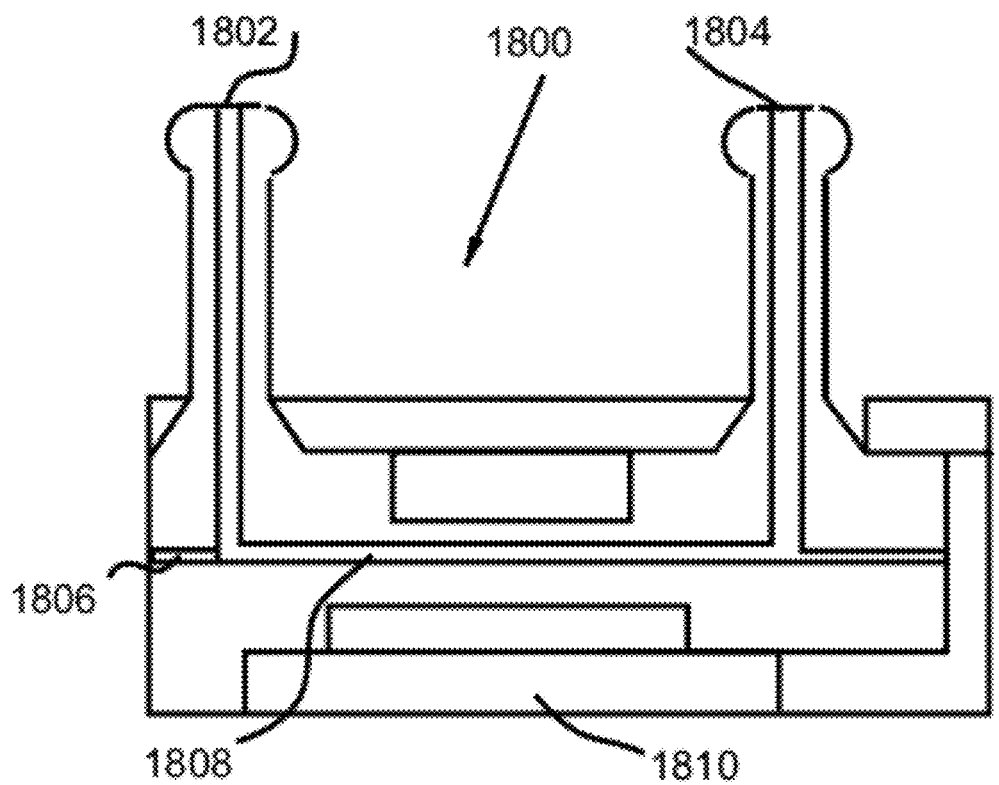

FIG. 18A. Side-view of the proposed sample cell with 1-10 um thickness for biological material.

Figure 18B:
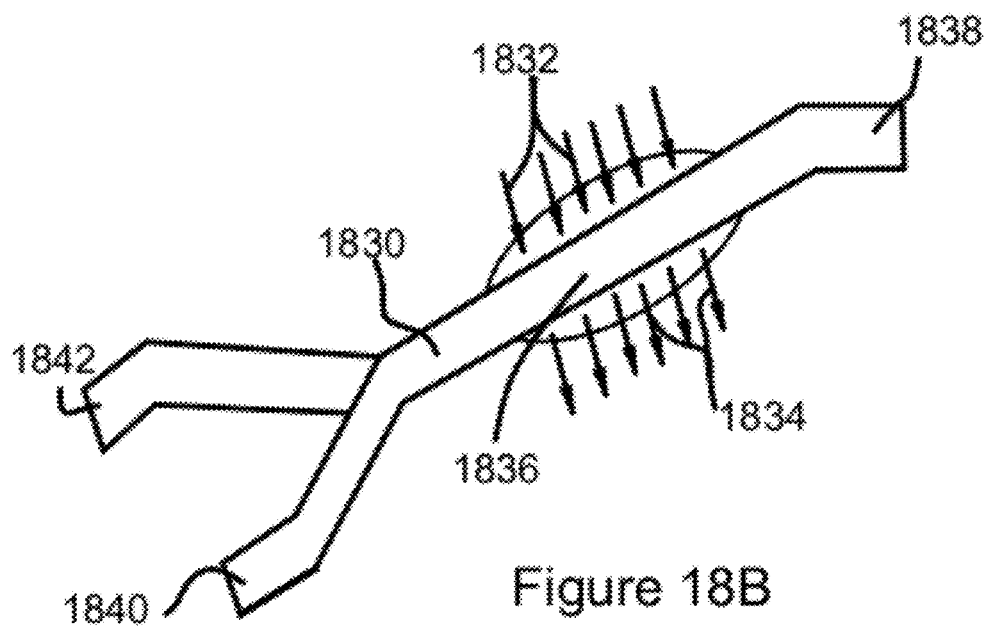

FIG. 18B. Schematic top view of fluidic system with multiple inlets to affect local chemical changes to biomolecule conformation and its integration to terahertz (THz) optics and detection.

Figure 19A:
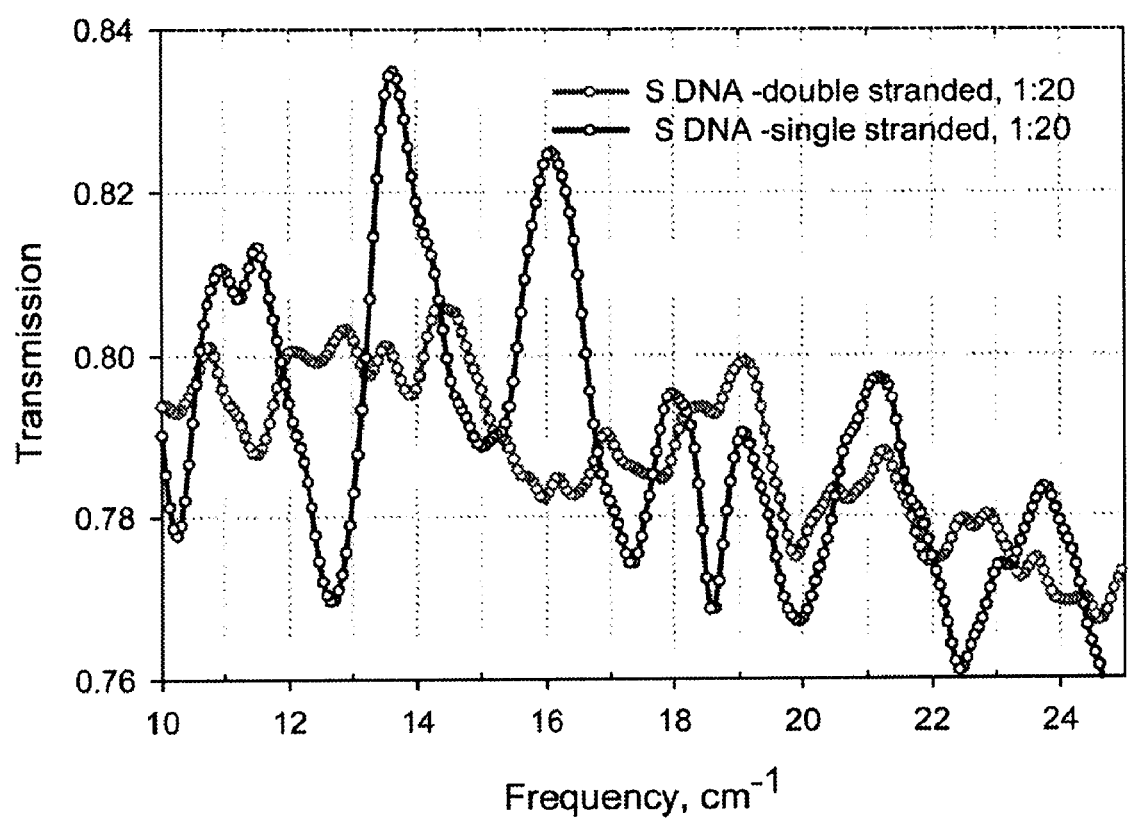
Figure 19B:
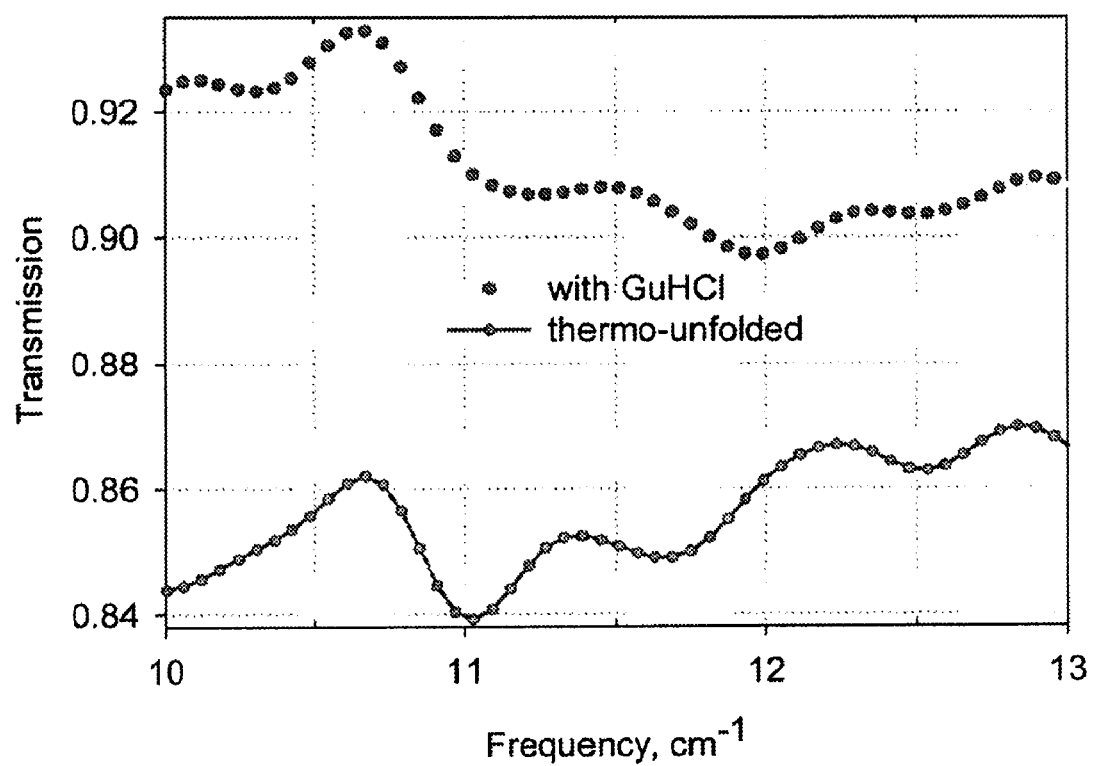

FIG. 19A. Sub-THz transmission spectra of a single stranded and double stranded Salmon DNA. The sensor can be tuned to either of frequencies 12.7 $cm^{-1}$, 16 $cm^{-1}$, or 22.3 $cm^{-1}$ where spectral features differences are observed [30];

FIG. 19B. Lysozyme unfolded with a GuHCl and thermo-unfolded. Lysozyme sample unfolded with GuHCl are in substantially unfolding state in which little persists secondary or tertiary structure and eliminates refolding process in unfolded lysozyme.

Figure 20:
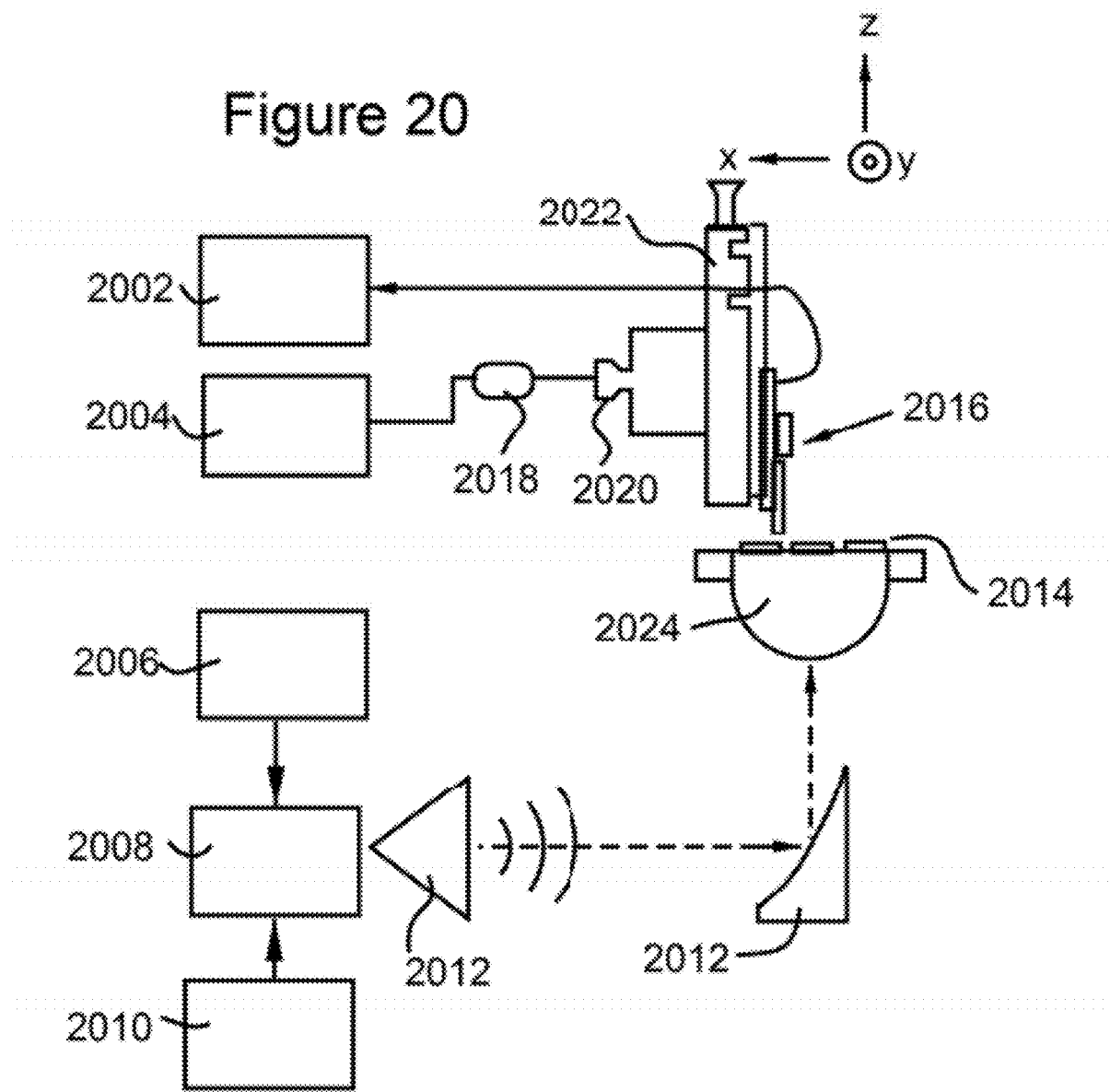

FIG. 20. The schematic layout for the experimental system.

DETAILED DESCRIPTION OF THE INVENTION

Definitions

As employed herein, the term "slots" is inclusive of a structure having a linear array of thin opaque strips, a structure in which slots are formed in a solid material, and slits or slots having a periodic spacing and suspended on a solid matrix. The term slots is inclusive of hole and gratings. The geometry of slots includes:

a closed curve, the intersection of a right circular cone (see cone) and a plane that is not parallel to the base, the axis, or an element of the cone. It may be defined as the path of a point moving in a plane so that the ratio of its distances from a fixed point (the focus) and a fixed straight line (the directrix) is a constant less than one. Any such path has this same property with . . .

elongated slot, such as, a flattened circle: a two-dimensional shape like a stretched circle with slightly longer flatter sides ii—Egg Shape: something shaped like an egg or a flattened circle iii—Oval—a closed plane curve resulting from the intersection of a circular cone and a plane that is non-parallel to the plane of the base of cone the cutting completely through it; "the sums of the distances from the foci to any point on an ellipse is constant".

Ellipse:

A conic section whose plane is not parallel to the axis, base, or generatrix of the intersected cone.

The locus of points for which the sum of the distances from each point to two fixed points is equal.

A four sided polygon having opposing sides equal to each other but not equal to their adjacent sides.

An elongated square or rectangle.

A rectangle with rounded corners viii—An Elongated Parallelogram—a quadrilateral whose opposite sides are both parallel and equal in length to each other but not equal in length to adjacent sides Description An aspect of various embodiments of the present invention comprises, but is not limited thereto, a method and related system for detection of the THz spectroscopic signatures of bio-molecules or other materials of interest, such as explosives, in 0.1-3 THz range that is based on the local EM field enhancement with respect to the incident field in structures with slot or slot arrays fabricated using semiconductor or metallic films or multilayer structures. This enhancement leads to an increased coupling of EM radiation in the THz spectral range to materials of interest and, therefore, results in dramatic improvements to the sensitivity, selectivity, reliability and spatial resolution of THz detection systems.

A prototypical embodiment of this application to deliver the enhanced coupling of THz radiation with bio- or chemical materials is through periodic structures of sub wavelength slots in semiconductor or metallic films. In the THz region, interaction between radiation and metals is quite different from higher frequency regions due to the change in material dielectric properties. In the visible and near-IR regions, where frequencies are only slightly less than plasma frequency, the permittivity is predominantly real and negative (for example, at wavelength 1 μm, $\in_{Au}=-51.4+j1.6$), and metals are reflective. On the contrary, as the frequency is lowered to the THz range, the real part continues to be negative and large, but the dissipative imaginary part becomes larger, and hence metals are very conducting and absorbing (at wavelength 500 μm, $\in_{Au}=-5.5\times10^4+j8.5\times10^5$). Therefore, to reduce radiation losses, it is preferable to substitute metals with doped semiconductors with plasma frequencies in the low THz range. InSb with high electron mobility and low effective mass is most suited for this purpose, but still has a substantial absorbing imaginary part compared to the real component. In the semiconductor structure with periodic gratings, the material properties are periodic functions of coordinates as well. The absorbing component in semiconductors (InSb and Si) requires the assumption of a small film thickness, which makes the semiconductor skin depth at both semiconductor-air interfaces larger than half the film thickness throughout the frequency range of interest. This renders the surface impedance boundary conditions for perfect conductors [32, 33] to be unsuitable for semiconductor structures. On the other hand, in contrast with the behavior of metals in short wavelength ranges, the Fourier expansion method for field diffracted from gratings [9] can be applied in the THz region for InSb and Si films, since the imaginary permittivity component damps the Gibbs oscillations [34]. The Fourier expansion of the electro-magnetic fields and the permittivity were used to solve the terahertz transmission/absorption/reflection problem and to calculate the total distribution of the electro-magnetic field in the system. At the same time, the Fourier expansion method is unsuitable for Au owing to its dielectric properties. However since the skin depth for Au is small compared to thickness, surface impedance boundary conditions can be used. Even in this case, the perfect conducting walls approximation [35] for fields inside slots is employed since the thickness assumed is very small compared to the wavelength. Using a rigorous theoretical model of the enhancement effect derived from the numerical solution of Maxwell's equations for semiconductor based periodic structures with one dimensional slot arrays in 0.3-0.75 THz range [described originally in Refs. 5, 6], the "edge effect", a localization of EM field that can be used to implement novel bio- and chemical sensors, was discovered. Maxwell's equations with appropriate boundary conditions on interfaces were solved with the frequency-dependent permittivity of the doped semiconductor. For polar materials like InSb, the frequency dependence of the relative permittivity, $\in(\omega)$, includes terms describing the interaction of light with free carriers (Drude model) and with the optical phonons.

Example

Figure 1:
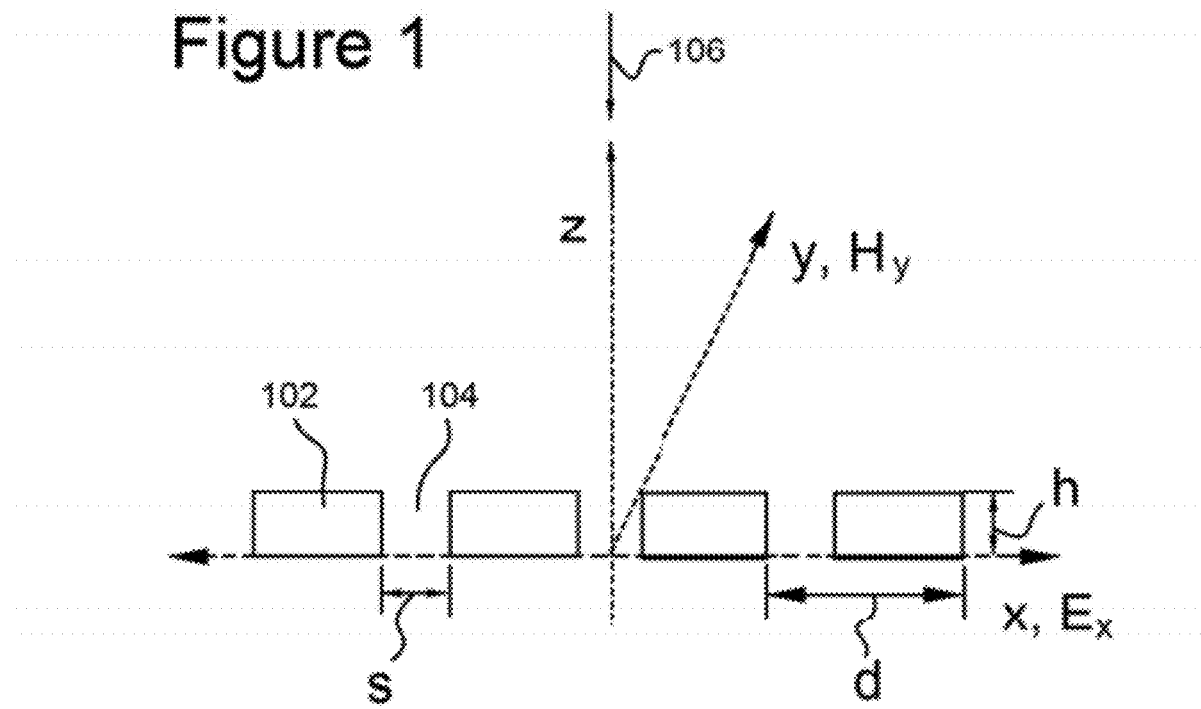
FIG. 1. The periodic rectangular slot array structure. The axes and the structure parameters (d—spacing, s—slot width, h—film thickness) are shown. The vector of electric field is in the x direction perpendicular to the slot.

An aspect of various embodiments of the present invention can comprise a structure suitable for sensing applications, as illustrated in FIG. 1. The structure includes a structure 102 having a subwavelength array of slots 104 with the periodicity in the x-direction and extending in the y-direction. The z-direction is perpendicular to the plane of incidence. Since the structural geometry is not altered in the y-direction, it would suffice to analyze a one-dimensional periodic slot structure as shown in FIG. 1 with spacing (or periodicity) denoted by (d), the slot width by (s) and the thickness of the film by (h). The structure is considered to be illuminated at normal TM incidence 106.

FIG. 2 shows the electric field amplitude (with incident field normalized to unity) at the interface of incidence, as a function of position with a slot width(s) of 55 µm, periodicity (d) of 381 µm, height (h) of 4 µm. The simulation frequency is chosen to be 420 GHz (wavenumber of 14 cm$^{-1}$) because absorption peaks of interest for many biological molecules have been shown to occur in this region. The enhancement of the field intensity at this frequency was obtained at all points in the slots. The half-power peak field near the slot edges occurs over a sub-micron region (~500 nm). In practice, most of the field is confined to the edges (i.e. sharp regions) of the conducting medium. The maximum power enhancement is approximately 1100 and also occurs for a slot height of 4 µm. The enhancement persists across the slots, decreasing slightly from the incident interface to the outgoing (transmission) interface. It cannot be attributed to a surface plasmon mode because the plasmon matching condition is not applicable for permittivities with substantial imaginary parts.

Using InSb as an example, it has been shown that the 30-fold EM field enhancement within the sub-micron region of the slot edges, translates into a 1000 fold increase in power (FIGS. 2 and 3). This "edge effect" at sub-THz frequencies caused by discontinuity effects is an important new result that can be applied to guide designs for enhanced THz coupling, as described below. The EM field enhancement at other points inside the slot, away from the edges is smaller, on the order of 3-5 fold. The enhancement of the amplitude of the electric field with respect to the incident field is demonstrated in FIG. 2 where the relative x-component of the electric field amplitude is plotted as a function of a coordinate across the slot, x, with s=55 µm and h=4 µm, for radiation with the frequency of 14 cm$^{-1}$. The electric field enhancement occurred within the sub-micron region around the slot edges i.e. at discontinuities as illustrated in FIG. 2. Practically most of the fields were confined to the edges i.e. sharp regions of the conducting medium. The enhancement at the edges is an order of magnitude higher than at the other points within the slot. The maximum field enhancement is 33.3 at the incident interface and 31.8 at the outgoing interface for h=4 µm. For h=6 µm, these values are 27.7 and 25 respectively and for h=12 µm, 20.5 and 14.7 respectively. The half power width around the slot edges was ~500 nm with maximum power enhancement ~1100 for the h=4 µm case. This region did not change much for the other h values. The enhancement exists across the slots, slightly decreasing from the incident interface to the outgoing interface. The decay into the metallic region is more abrupt than into free space as expected, as seen in FIG. 3, and around the edges is approximately proportional to $\chi^{-1/3}$, consistent with edge effects.

FIG. 3 illustrates the basic concept of an instrument of the present invention. FIG. 3 shows THz power, $(E_x/E_o)^2$, enhancement as a function of a coordinate x (µm) across a slot for the structure with the same parameters as in FIG. 2 at two frequencies 14 cm$^{-1}$ (the wavelength $\lambda$=714 µm) and 24 cm$^{-1}$. It is seen that an imaging sensor is capable of measuring the THz response as well as resolving spatial features of samples under the test with a micron-submicron resolution. The instrument employs a terahertz source radiation that is collimated using optical components. The THz radiation is directed at a thin film slot grating integrated with a microfluidic channel with the sample material to be measured where the sample is illuminated with the terahertz energy. An integrated THz micro-detector assembly is composed of three essential parts, i.e. a sub-micron probe (antenna) that is connected to a miniature bolometer detector (for example, Schottky-diode), and control circuit with the corresponding impedance matching network to achieve the precise detection of the electric field in the near-field configuration. The detector assembly with a micro probe is mounted on the stage, which provides precise scanning, with a resolution of less than 1 µm, over the sample under test along XYZ direction with nanometer accuracy controlled by the control circuit.

The technology for fabricating the miniature detector with micron size antenna to affectively couple with THz radiation transmitted through the slit is disclosed in publications noted herein as 26 and 27.

FIG. 4 compares the enhancement of two electric field components, $E_x$ and $E_z$, that are perpendicular and along the direction of the incident radiation. The enhancement at the slot edge as a function of a slot width is plotted in FIG. 5 for three different thickness. The calculated far field transmission through the structure is plotted in FIG. 6 as a function of a periodicity, d/$\lambda$, for different slot widths. The "edge effect" at sub-THz frequencies for two other materials (silicon and gold) is demonstrated in FIGS. 7A and 7B. The effect is significantly less than for InSb structure, however these materials still can be used due to technological advances. In all these cases, a sub micron narrow THz beam along the edge is a local, highly intense radiation source for probing biological and other material properties using near field configuration for specific microscopic sensing and imaging instruments in the THz range.

The invention is illustrated by the example structure consisting of a one-dimensional array of rectangular slots with the period less than the wave length λ of applied EM radiation, which contains small quantities of biological material embedded in the nano-size regions of the edges where enhancements of radiation in the THz gap are observed. This array is made of a thin-doped InSb film with a free electron concentration of $1.1 \times 10^{16}$ cm$^{-3}$ fabricated on a substrate transparent for THz radiation. This is not to be construed in any way as imposing limitations upon the scope of the invention. Structures with slot arrays or hole arrays of different periodicity and different geometry can be used as well. Different materials such as semiconductor films or metallic films can be used separately or in combinations as in multilayer structures.

It should be understood that resort can be had to various other embodiments, modifications, and equivalents to the embodiments of the invention described herein which, after reading the description of the invention herein, can suggest themselves to those skilled in the art without departing from the scope and spirit of the present invention.

FIG. 8 shows an embodiment of the present invention for the application of the periodic array of semiconductor slots to enhance THz coupling to materials of interest for THz sensing and imaging. The basic concept of the instrument is an imaging instrument capable of measuring the THz spectral response as well as resolving spatial features of samples under test with submicron resolution. The design consists of three parts:

A supporting plate from plastic or quartz onto which a periodic slots structure is bonded or electroplated that also comprise materials sample chamber;

A miniaturized THz detector assembly which can be adjusted with a movable stage so that sub micron probe(s) of detector(s) are within ~1 μm of the plane where the THz radiation exiting the slots. The preferable miniaturized THz detector is a Schottky micro-diode from Virginia Diode Inc., Charlottesville, Va., integrated with a coupling circuit and a nano-probe (antenna); and a motorized movable stage with controller that provides sub micron steps.

A terahertz source is collimated using standard optical components onto the sample material that is induced into channels of a microfluidic periodic structure integrated with a thin film periodic slot grating. The detector assembly with a micro probe is mounted to an XYZ nanopositioner and is scanned over the sample under test. High-resolution piezoelectric positioners with nanometer accuracy and travel ranges up to 1 cm are commercially available and can be used for probe placement and positional control.

In this configuration, the rectangular slots of a periodic structure are concurrently used as channels for the sample material and the materials or molecules of interest can be immobilized on the surface of the film structure or trapped at the slot edges.

In another embodiment, these two functional elements can be separated. Small quantities of biological material are embedded in the nano-size regions of the edges where enhancements of radiation in the THz gap are observed. Very small amount of material would be enough for detection using this approach. The detector probes (antennas) can be scanned in two perpendicular directions across the sample chamber and sample material to improve sensitivity and selectivity of THz sensing or to generate a 2D THz imaging.

Such application modes provide a new class of devices using bio- or chemical fluidic chips combined with near field THz detectors.

The effect of local near field enhancement of electromagnetic field is used to maximize the coupling of terahertz radiation to both biological and chemical molecules. The new process for coupling provides dramatic improvements in spatial resolution, sensitivity, reliability, and selectivity of terahertz detection systems. The imaging mechanism of the present invention is appertureless, all optical, and utilizes low THz frequency range radiation to achieve a spatial resolution well below the diffraction limit.

This new detection platform can produce a new class of resonant, highly sensitive and selective portable bio and chemical devices for uses in many different applications. By interacting the THz vibration absorption modes from organic or biological molecules with a locally enhanced EM field of terahertz radiation in a sub-micron region, the developed imaging mechanism:

Is capable of sub wavelength spatial resolution, ideally $10^3$ orders less than the radiation wavelength.

Is an all-optical instrument, with no required mechanical tips or probes to contact testing material.

Requires no apertures.

Can allow for spectral selectivity.

Can test biological monolayers, and molecules in dilute solutions.

The applications of terahertz frequencies for identification and detection uses is virtually almost endless, ranging from military and transportation detection devices to real time drug development monitoring of anti-bacterial or anti-viral drugs.

Some Examples

New imaging mechanism integrated with a "lab-on-a chip" device for sub-wavelength THz spectroscopic microscope.

Water quality monitoring.

Monitoring biological processes

Real time monitoring of drug-bacteria cell wall interaction in drug development.

Rapid tissue testing for skin cancer diagnostics

Portable bio-material structure testing devices.

The research work included sensor modeling and design, fabrication of a beam lead antenna and a diode integrated with a circuit, and demonstrated the successful implementation of the imaging mechanism of the present invention. All elements of a THz detector assembly to measure the electrical field distribution around the periodic slots were modeled and fabricated and the detector assembly was completed and tested.

The periodic slots structure of FIG. 9, indicated generally as 900, was made of gold thin film on silicon wafers and quartz using the photolithographic process and electroplating. The key challenge associated with the fabrication of the slot arrays 902 is to obtain a high degree of sharpness at the edges of slots due to the fact that the enhancement of electrical field is in a micron region. The microfabrication processes have been optimized to obtain high sharpness at the edge 1002 of the slots 1006, as shown in FIG. 10. The edge extrude of 0.2-0.5 μm has been attained.

The key function of the THz micro-sensor is to detect the electrical field in the vicinities of the slot edges where the enhanced coupling occurs. In other word, the THz micro-sensor system is responsible to detect the near field distribution of radiation transmitted through the biological or other materials of interest that are located around the edges of the slots. Since the electrical field enhancement is only available in a region of several microns, the sub-micron sharp probe (antenna) 1102 of FIG. 11, is required for the sensing of the transmitted electrical field through biological sample in order to obtain high sensitivity and spatial resolution. Thus, it is crucial to provide an integrated THz sensor detector with high-sensitivity and sub-micron spatial resolution for sub-wavelength THz spectroscopy.

One example of such a sensor is a miniature sensing device which incorporates a room-temperature detector, Schottky micro-diode 1112, integrated with a coupling circuit and a nano-probe 1108, (also referred to as an antenna) mounted on a silicon substrate 1102, as shown in FIG. 11A. Other types of miniature detectors can be used as well.

The zero biased Schottky diode 1112, which in this example incorporates GaAs islands, transforms the input THz radiation coupled from the sharp beam lead probe 1108 tip to the output dc voltage. The magnitude of the output dc voltage is proportional to the input power of the THz radiation. In FIG. 11*b*, a low pass filter 1120 and the RF choke 1126, are the components for blocking the high frequency radiation for the measurement of the dc voltage across the diode 1112. Thin (50 μm) fused quartz material is chosen as the substrate 1102 for the detector circuit to minimize the possible surface mode excitation. The detector assembly chip in this example is 1 mm wide and 1.5 mm long. As illustrated in FIG. 12 the beam lead micro-tip 1200 has a length of about is ~60 μm long, as indicated by arrow 1204, has a tip length of about 15 μm as indicated by arrows 1206, a tip width of about 15 μm as indicated by arrow 1202, and a tip 1208 of about 0.64 μm. Other types of miniature detectors that produce the same results as the detector set forth above can be used as well.

A sharp coupling device can modify the original electrical field distribution produced by the slots structure. Thus, the size of the coupling device and the distance between the coupling device and the slots has to be designed and optimized in order to obtain the balance between measurement and disturbance of the local electrical field around the periodic slots, while being a physically realizable tip geometry. The local electrical field enhancement at the edge of slot is confirmed by our electrical field simulation work using the commercial full-wave solver. From FIG. 13 it is seen that although the beam lead antenna disturbs the electric field distribution, the enhancement effect near slot edges is preserved.

Another aspect of the research was fabrication and characterization of sample or microfluidic chambers. To apply the local enhancement of THz coupling, the bio- or chemical material can be immobilized on the surface, trapped at slot edges, or scanned across a microfluidic chamber. The materials of interest can be in solid or fluidic form. Microfluidic channels were fabricated using polydimethylsiloxane (PDMS) as the polymeric material onto which channels were micromolded. Inexpensive disposable periodic Lab-on-chip structures can be used for enhanced THz coupling and detection.

The slots can be scanned across the material sample to enhance local coupling and thereby improve the chemical resolution and sensitivity of the detector to THz imaging. The linear array of several integrated THz sensor detectors can be designed and fabricated to provide the capability for a two-dimensional imaging. One of possible solutions for realization a proposed imaging technology is to use a linear detector array of micron/sub-micron size detector elements with a coupling structure, antenna, at each element to probe several slots. Only short distance movement of the detector assembly over the slot width will be required in this case.

FIGS. 14 and 15 demonstrate the existing capabilities to fabricate a Schottky diode or bolometer detector array with the spacing between elements ~40 μm [27, 28]. FIG. 15 illustrates an array section 1500 including low band pass filters 1504 and slot ring antennas 1502, and an HEB superconducting bridge 1506.

FIG. 16 shows (not in scale) an example of a detector assembly 1606 combined with a sample or microfluidic channel 1612 (5-50 μm wide, 1 μm deep, 1-2 cm long), with a 10-50 μm transparent substrate, that is, a backing support 1610 to enable handing, is filled with bio-material 1604. In this embodiment a 2-5 μm Au edge layer 1602 is patterned on the top of channel structure, although other semiconductors as taught herein can be used. A movable stage with an XYZ controller 1608 is placed at one end of the channel 1612. As can be seen, linear polarized THz radiation 1614 is presented at right angles to the substrate 1610.

The precise control of the THz sensor position, especially of the sensing probe, has to be implemented in order to enable the sensor to approach near the surface of a sample and to scan along the plane of the periodic structure. Long focused optical components can be utilized for precise location of sensing antennas at the distance of about 1-3 μm from the sampling material. Electric (for example, capacitive) sensors can be used as well.

The disclosed detection system can include variety of miniaturized THz near-field sensors as listed above. Another application of the invention is monitoring changes of dielectric properties of bio-materials in biophysical processes, for example, denaturation of DNA, folding-unfolding of proteins, structural conformational changes of biomolecules in interactions with drags, and monitoring other processes for a broad bio-medical and pharmaceutical research.

FIG. 17 illustrates a detection device 1700 wherein the THz illumination 1701 is applied from the top down. A plate of quartz 1710 has InSb 1712 bonded to the plate 1710 effectively forming slots 1714. The mid-plate 1720 contains the fluidic cells 1722 with an inlet and outlet. The mid-plate 1720 is adjacent to the quartz bottom plate 1730 that contains a translatable piezo stage with THz detectors. The near field detectors can be less than 0.1 μm from the fluidic cells.

FIGS. 18A and 18B are illustrative arrangements for the microfluidic cells. In FIG. 18A the cell 1800 has an inlet 1802 that is connected to an outlet 1804 by channel 1808. In FIG. 18B the biomolecules enter the cell at inlet 1 (1842) and the reagent at inlet 2 (1840) and are mixed at the joining point 1830. The biomolecules are moved into the trapping region 1836 where they are exposed to THz radiation 1832. A THz detector receives the resulting radiation 1834. The biomolecules then move to the outlet 1838. The cell can be used for real time monitoring of processes.

FIG. 19 demonstrates the dramatic difference in transmission spectra of a single and double-stranded DNA that can be used in the proposed monitors. FIG. 19*a* shows similar possibilities for monitoring conformational change of proteins.

FIG. 20 shows the schematic layout for the experimental system.

The system composes of

THz source (GHz signal generator 2010, frequency multiplier 2008 and power supply 2006 for the source);

collimating devices 2012 (an off-axis parabolic mirror 2012 and an hemispheric silicon lens);

horn 2012;

periodic slot chip 2014 combined with microfluidic cell and mounted on the planar surface of silicon lens 2024;

detector assembly chip 2016 (beam lead probe, transmission line, Schottky diode and detector circuit);

motorized XYZ stage with controller 2022;

the dc voltage measurement device (i.e. a lock-in amplifier) 2002, and controlling computer 2004.

The THz radiation required to illuminate the periodic structure is generated by multiplying the low frequency radiation using a frequency multiplier (36 times) as can be obtained from a source such as Virginia Diodes Inc., of Charlottesville Va. System path loss is minimized by using reflectors (rather than lens) as well as an anti-refection coating on the surface of the hemispherical lens. The lens assembly is mounted to a platen. The integrated THz antenna is scanning transmitted beam over the sample material put into a microfluidic channel using precision XYZ positioners.

Some exemplary products and services that various embodiments of the present invention method and system may be utilized for may comprise, but not limited thereto, the following:

Transportation Security:

Portable scanners to detect explosive residues or bio hazards on clothing, bags, in vehicles, in trains, metro stations, airports, on board of ships, on bridges, in tunnels.

Public Safety:

Portable scanners to detect explosive residues or bio hazards in public areas, buildings.

Quality of water monitoring.

Military

Compact remote sensors to detect explosives or bio hazards that can be installed as stand alone devices, as well as on buildings, structures, put on unmanned airplanes, unmanned land vehicles.

Light weight battlefield detectors that can be carried by soldiers.

Drug Development:

Detectors for real-time monitoring of drug-bacteria cell wall interaction, for testing the effectiveness of bacteria or virus destruction by drugs under development.

Medicine

Rapid tissue testing, cell testing for skin cancer diagnostics.

Biomaterial Applications

Portable devices for biomaterial structure testing.

The following publications as listed below and throughout this document are hereby incorporated herein by reference in their entirety.

[1] T. Globus, D. Woolard, M. Bykhovskaia, B. Gelmont, L. Werbos, and A. Samuels, Int. J. of High Speed Electron. Syst. 13, 903 (2003).

[2] T. Globus, D. Woolard, T. W. Crowe, T. Khromova, B. Gelmont, and J Hesler, J. Phys. D: App. Phys. 39, 3405 (2006).

[3] A. Bykhovski, T. Globus, T. Khromova, B. Gelmont, and D. Woolard, Proc. SPIE 6212, 62120H (2006).

[4] Proposal submitted to DARPA, Solicitation Number: BAA06-19, "Terahertz characterization for real time control protein conformation." T. Globus, PI. Jul. 11, 2006.

[5]. R. Parthasarathy, A. Bykhovski, Boris Gelmont, T. Globus, N. Swami, D. Woolard, "Enhanced coupling of sub-terahertz radiation with semiconductor periodic slot arrays", Phys. Rev. Lett., 98 (15), 153906 (2007).

[6]. B. Gelmont, R. Parthasarathy, T. Globus, A. Bykhovski, and N. Swami, "Terahertz (THz) Electromagnetic Field Enhancement in Periodic Subwavelength Structures", The 2007 Nanoelectronic Devices for Defense & Security (NANO-DDS) Conference Presentation, Washington D.C., June 2007, submitted to the IEEE Sensors Journal Special Issue.

[7]. A. Sommerfeld, *Optics*. Academic Press Inc., New York, 1954.

[8]. M. E. McDonald, A. Alexanian, R. A York, Z. Popovic, and E. N. Grossman, "Spectral Ttransmittance of Lossy Printed Resonant-Grid Terahertz Bandpass Filters", *IEEE Trans. on Microwave Theory and Techniques*, vol. 48, pp. 712-718, April 2000.

[9]. *Electromagnetic Theory of Gratings* edited by R. Petit, Springer-Verlag, Berlin Heidelberg, 1980.

[10]. Sheng, R. S Stepleman, and P. N. Sanda, "Exact eigenfunctions for square-wave gratings: Application to diffraction and surface-plasmon calculations", *Phys. Rev. B*, vol. 26, pp. 2907-2916, 1982.

[11]. H. E. Went, A. P. Hibbins, J. R. Sambles, C. R. Lawrence, and A. P. Crick, "Selective transmission through very deep zero-order metallic gratings at microwave frequencies", *App. Phys. Lett*, vol. 77, pp. 2789-279, 2000.

[12]. Q. Cao, and P. Lalanne, "Negative Role of Surface Plasmons in the Transmission of Metallic Gratings with Very Narrow Slits", *Phys. Rev. Lett*, vol. 88, pp. 057403-01-04, 2004.

[13]. T. W. Ebbesen, H. J. Lezec, H. F. Ghaemi, T. Thio, and P. A. Wolff, "Extraordinary optical transmission through sub-wavelength hole arrays", *Nature*, vol. 391, pp. 667-669, 1998.

[14]. H. F. Ghaemi, T. Thio, D. E. Grupp, T. W. Ebbesen, and H. J. Lezec, "Surface plasmons enhance optical transmission through subwavelength holes", *Phys. Rev. B*, vol. 58, pp. 6779-6782, 1998.

[15]. T. Thio, H. F. Ghaemi, H. J. Lezec, P. A. Wolff, and T. W. Ebbesen, "Surface-plasmon-enhanced transmission through hole arrays in Cr films", *J. Opt. Soc. Am B*, vol. 16, pp. 1743-1748, 1999.

[16] E. Popov, M. Neviere, S. Enoch, and R. Reinisch, "Theory of light transmission through subwavelength hole arrays", *Phys. Rev. B*, vol. 62, pp. 16100-16108, 2000.

[17]. L. Martin-Moreno, F. J. Garcia-Vidal, H. J. Lezec, K. M. Pellerin, T. Thio, J. B. Pendry, and T. W. Ebbesen, "Theory of Extraordinary Optical Transmission through Subwavelength Hole Arrays", *Phys. Rev. Lett*, vol. 86, pp. 1114-1117, 2001.

[18]. A. Darmanyan, and A. V. Zayats, "Light tunneling via surface plasmon polariton states and the enhanced transmission of periodically nanostructured metal films", *Phys. Rev. B*, vol. 67, pp. 035424-1-7, 2003.

[19]. S. H. Chang, and S. K. Gray, "Surface plasmon generation and light transmission by isolated nanoholes and arrays of nanoholes in thin metal films", *Opt. Exp.*, vol. 13, pp. 3150-3165, 2005.

[20]. H. Cao, and A. Nahata, "Resonantly enhanced transmission of terahertz radiation through a periodic array of subwavelength apertures", *Opt. Exp.*, vol. 12, pp. 1004-1010, 2004.

[21]. D. Qu, D. Grischkowsky, and W. Zhang, "Terahertz transmission properties of thin, subwavelength metallic hole arrays", *Opt. Lett.*, vol. 29, pp. 896-898, 2004.

[22]. J. Gomez Rivas, C. Schotsch, P. Haring Bolivar, and H. Kurz, "Enhanced transmission of THz radiation through subwavelength holes", *Phys. Rev. B*, vol. 68, pp. 201306-1-4, 2003.

[23]. J. Gomez Rivas, C. Janke, P. Haring Bolivar, and H. Kurz, "Transmission of THz radiation through InSb gratings of subwavelength apertures", *Opt. Exp.*, vol. 13, pp. 847-859, 2005.

[24]. J. W. Lee, M. A. Seo, D. J. Park, S. C. Jeoung, Q. H. Park, C h. Lienau, and D. S. Kim, "Terahertz transparency at Fabry-Perot resonances of periodic slit arrays in a metal plate: experiment and theory", *Opt. Exp.*, vol. 14, pp. 12637-12643, 2006.

[25]. E. Popov, S. Enoch, G. Tayeb, M. Neviere, B. Gralak, and N. Bonod, "Enhanced transmission due to non-plasmon resonances in one- and two-dimensional gratings", *App. Opt.*, vol. 43, pp. 999-1008, 2004.

[26]. VIBRATESS, LLC. ARO SBIR Phase I Final Report "Spectroscopic Imaging Technology for THz Biosensor Integrated with a Lab-on-Chip Platform", Contract #: W911NF-07-C-0055, December 2007.

[27]. Interim Report for the UVA-Keck Project "Terahertz Spectroscopy of Biological Molecules:Developing THz prototype spectrometer for bio-medical research" for the period of January 2006-December 2007.

[28]. D. S. Kurtz, J. L. Hesler, J. B. Hacker, T. W. Crowe, D. B. Rutledge, and R. M. Weikle, II, "Submillimeter Wave Sideband Generation using a Planar Diode Array"; IEEE MTT-S Internat. MicrowaveSymposium Digest, vol. 3, pp. 1903-1906, Baltimore, Md., June 1998.

[29]. L. Liu, H. Xu, Q. Xiao, A. W. Lichtenberger, and R. M. Weikle, II, "Performance at 585 GHz of a Slot RingAntenna Coupled Niobium HEB Mixer Element for Imaging Applications"; Proceedings of the Joint 30th International Conf. On Infrared And Millimeter Waves and the 13th International Conference On Terahertz Electronics, Williamsburg, Va., pp. 265-266, September 2005.

[30]. T. Globus, A. Bykhovski, B. Gelmont, R. M. Weikle, J. O. Jensen, W. R. Loerop, "Enhanced Spectroscopy Signatures of Biological Molecules and Organisms in the Low THz Range". The 2007 Scientific Conference on Chemical & Biological Defense Research, Timonium, Md., 13-15 Nov. 2007.

[31]. T. Globus, T. Khromova, R. Lobo, D. Woolard, N. Swami, and E. Fernandez, "THz characterization of lysozyme at different conformations", Proceedings of SPIE, "Terahertz for Military and Security Applications", v. 5790, p. 54-65, Defense and Security Symposium, Orlando, Fla., 28-29 Mar. 2005.

32. J. A. Porto, F. J. Garcia-Vidal, and J. B. Pendry, "Transmission Resonances on Metallic Gratings with Very Narrow Slits", Phys. Rev. Lett, vol. 83, pp. 2845-2848, 1999.

33. F. J. Garcia-Vidal, and L. Martin-Moreno, "Transmission and focusing of light in one-dimensional periodically nanostructured metals", Phys. Rev. B, vol. 66, pp. 155412-1-10, 2002.

34. G. B. Arfken, and H. J. Weber, Mathematical Methods for Physicists Academic Press, San Diego, Calif., $4^{th}$ ed, Chaps. 14, p. 836, 1995.

35. A. Wirgin, T. Lopez-Rios, "Can surface-enhanced Raman scattering be caused by waveguide resonances", Opt. Commun., vol. 48, pp. 416-420, 1984.

It should be appreciated that aspects of various embodiments of the present invention method and system may be implemented with the method and system disclosed in the following, the disclosures of which are incorporated herein by reference, as though recited in full:

U.S. Pat. No. 6,977,767 Plasmonic nanophotonics methods, materials, and apparatuses;

U.S. Pat. No. 7,170,085 Frequency selective terahertz radiation detector; and

U.S. Pat. Application Publication No. 2005/0230705 A1 to Taylor, Geoff W.

What is claimed is:

1. Method of enhanced THz coupling to molecules, comprising the steps of:

depositing a test material near the discontinuity edges of a slotted member, enhancing said THz radiation by transmitting THz radiation through slots in said slotted member, illuminating molecules of said test material with said enhanced THz radiation transmitted through said slots, thereby producing an increased coupling of EM radiation in the THz spectral range to said material.

2. The method of claim 1, wherein said enhanced THz radiation is an EM field of terahertz radiation in a submicron region and further comprising analyzing the THz vibration absorption by said test material.

3. The method of claim 1, wherein said molecules comprise bio-molecules, organic molecules, or an explosive.

4. The method of claim 1, wherein said slotted member being selected from the group comprising doped semiconductors, metal films, and multilayer structures that support modes that locally enhance EM fields, and near field sensing of THz radiation from said molecules, wherein increased coupling and spatial resolution are both based on the local EM field and power enhancement near the discontinuity edges with respect to the incident field in slotted structures.

5. The method of claim 1, wherein the vector of said THz radiation is directed perpendicular to said slots.

6. The method of claim 1, further comprising generating EM field enhancement at the edges of said slots, embedding a bio- or chemical material at the location of said enhanced EM field, transmitting said THz radiation through said slots and said bio- or chemical material at the location of said enhanced EM field, sensing near field THz radiation that has been transmitted through said slots and has illuminated said bio- or chemical material at the location of said enhanced EM field.

7. The method of claim 1, further comprising the step of near field scanning with a THz antenna, of transmitted radiation of a slotted member from sample material near said discontinuity edges.

8. The method of claim 1 wherein said transmitting of THz radiation through said slots increases the degree of the coupling of EM radiation in the THz spectral range to materials of interest by transmitting THz radiation through an array of openings, transmitting said THz radiation from said array of openings through bio- or chemical material and sensing near field THz radiation that has been transmitted through said slots and said material, and further comprising detection of the spectroscopic signatures of said bio- or chemical material.

9. Method of increasing coupling of EM radiation in the THz spectral range to weak bonds in molecules, comprising the steps of:

depositing a material near the discontinuity edges of slots of a slotted member, and transmitting THz radiation through said slots and illuminating said molecules with the transmitted THz radiation.

10. The method of claim 9, wherein said slots are periodic structures and increasing coupling due to the diffraction or discontinuity edge effects in propagation of THz radiation in subwavelength rectangular slots of said slotted member, said slotted member being fabricated from semiconductor materials, metals, or combinations thereof.

11. The method of claim 9, wherein said material comprises microscopic biological or chemical molecules, and further comprising the step of sensing near field THz radiation that has been transmitted through said slots and said bio- or chemical material.

12. The method of claim 9 wherein said material is selected from the group comprising explosives, toxic materials, living organisms, and pharmaceuticals.

13. Method of increasing coupling of EM radiation in the THz spectral range to weak bonds in molecules, comprising the steps of:

depositing a material near the discontinuity edges of slots of a slotted member, and transmitting THz radiation through said slots and illuminating said molecules with the transmitted THz radiation further comprising monitoring changes of dielectric property of bio-materials in biophysical processes, wherein said property is selected from the group comprising denaturation of DNA, folding-unfolding of proteins, and structural conformational changes of biomolecules in interactions with drugs, and further comprising the steps of:

generating a GHz signal, converting GHz radiation to THz radiation with a frequency multiplier, collimating said THz radiation for said step of transmitting THz radiation through said slots and illuminating said molecules with the transmitted THz radiation generating EM field enhancement at the edges of said slots;

selectively detecting enhanced THz transmitted through said bio-materials at said edges of said slots, monitoring said selectively detected enhanced THz radiation, and determining changes of dielectric properties of bio-materials in biophysical processes based on said monitored selectively detected enhanced THz radiation.

14. An all-optical, apertureless instrument, free of mechanical tips or probes to contact testing material, comprising a slotted member, having a periodic array of semiconductor slots, a source of THz radiation positioned to transmit THz radiation through slots in said slotted member, an analyte material embedded at least at the edges of the slots of said slotted member, means to illuminate said material with said THz radiation, and means to sense near field THz radiation from said analyte material at the edges of the slots.

15. An all-optical, apertureless instrument, free of mechanical tips or probes to contact testing material, comprising a slotted member, a source of THz radiation, an analyte material embedded at least at the edges of the slots of said slotted member, means to illuminate said material with said THz radiation, and means to sense near field THz radiation from said analyte material at the edges of the slots wherein said analyte material is molecules in dilute solutions and wherein said molecules are selected from the group comprising monolayers of biological material and cancer cells.

* * * * *